US007846672B2

(12) United States Patent
Rothenberg et al.

(10) Patent No.: US 7,846,672 B2
(45) Date of Patent: Dec. 7, 2010

(54) METHOD FOR DETECTING THE AFFINITY OF FOLATE RECEPTOR AUTO ANTIBODIES

(76) Inventors: Sheldon P. Rothenberg, 535 E. 86th St., New York, NY (US) 10028; Maria da Costa, 535 E. 86th St., New York, NY (US) 10028; Jeffrey Sequeira, 2360 62nd St., Brooklyn, NY (US) 11204; Edward V. Quadros, 232 76th St., Brooklyn, NY (US) 11209

( * ) Notice: Subject to any disclaimer, the term of this patent is extended or adjusted under 35 U.S.C. 154(b) by 572 days.

(21) Appl. No.: 10/534,303

(22) PCT Filed: Nov. 7, 2003

(86) PCT No.: PCT/US03/35690

§ 371 (c)(1),
(2), (4) Date: Nov. 1, 2005

(87) PCT Pub. No.: WO2004/043233

PCT Pub. Date: May 27, 2004

(65) Prior Publication Data

US 2006/0127955 A1 Jun. 15, 2006

Related U.S. Application Data

(60) Provisional application No. 60/424,965, filed on Nov. 8, 2002.

(51) Int. Cl.
*G01N 33/53* (2006.01)
*G01N 33/567* (2006.01)
*G01N 33/48* (2006.01)

(52) U.S. Cl. .................. 435/7.1; 435/7.2; 435/7.7; 435/40.51

(58) Field of Classification Search .................. None
See application file for complete search history.

(56) References Cited

U.S. PATENT DOCUMENTS

| 4,459,359 | A | * | 7/1984 | Neurath | 435/5 |
| 4,789,640 | A | * | 12/1988 | Lindstrom | 436/504 |
| 5,561,049 | A | * | 10/1996 | Vold et al. | 435/7.1 |
| 5,741,654 | A | * | 4/1998 | Michel et al. | 435/7.9 |
| 6,406,867 | B1 | * | 6/2002 | Yu et al. | 435/7.2 |
| 6,555,388 | B1 | * | 4/2003 | Boches et al. | 436/501 |
| 6,852,546 | B1 | * | 2/2005 | Brown | 436/506 |

FOREIGN PATENT DOCUMENTS

GB 2 103 363 A 2/1983

OTHER PUBLICATIONS

Hoier-Madsen et al., Rabbit antibodies against the low molecular weight folate binding protein from human milk. Use of immunological characterization of human folate binding proteins in an Ezyme-linked immunosorbent assay (ELISA). Bioscience Reports, 7, 553-557, 1987.*
Hoier-Madsen et al., Serum antibodies to cow's milk folate-biinding protein in patients with chronic inflammatory bowel disease. Int. J. Tiss. Reac. XI(6), 327-332,1989.*
Antony AC, The Biological Chemistry of Folate Receptors. Blood, 79, 2807-2820,1992.*
daCosta et al., Purification and charactherization of folate binding proteins from rat placenta. Biochim. Biophys. Acta, 1292, 23-30, 1996.*
Holm et al., Characterization of the Folate Receptor in Human Molar Placenta. Bioscience reports, 16, 379-389, 1996.*
Holm et al., High-Affinity Folate Receptor in Human Ovary, Serous Ovarian Adenocarcinoma, and Ascites: Radioligand Binding Mechanism, Molecular Size, Ionic Properties ,Hydrophobic Domain,and Immunoreactivity. Arch. Biochem and Biophys., 366, 183-191, 1999.*
Neuhouser M.L. et al., "Absorption of Dietary and Supplemental Folate in Women with Prior Pregnancies with Neural Tube Defects and Controls", *Journal of the American College of Nutrition* 17(6):625-630 (1998), XP008071060.
Hernández-Díaz S. et al., "Folic Acid Antagonists During Pregnancy and the Risk of Birth Defects", *The New England Journal of Medicine* 343(22):1608-1614 (2000), XP000989602.
Henderson G.B., "Folate-Binding Proteins", *Annual Review of Nutrition* 10:319-335 (1990), XP008071033.
de Costa M. et al., "Antibodies to Folate Receptors Impair Embryogenesis and Fetal Development in the Rat", *Birth Defects Research* 67(10):837-847 (2003), XP008071011.

* cited by examiner

*Primary Examiner*—Gary B. Nickol
*Assistant Examiner*—Elly-Gerald Stoica
(74) *Attorney, Agent, or Firm*—Scully, Scott, Murphy & Presser, P.C.

(57) ABSTRACT

The present invention identifies autoantibodies to folate receptors. Methods to identify these autoantibodies to the human folate receptors are also provided. The present invention also contemplates diagnostic methods and test kits to be used in a clinical setting for identifying a subject at risk of folate-sensitive abnormalities or disorders as observed in neural tube defect complicated pregnancies. In addition, infertility, spontaneous abortion, male sterility, unsuccessful in vitro fertilization, neurologic disorders and impaired folate absorption may also be associated with these autoantibodies to folate receptors.

10 Claims, 12 Drawing Sheets

Determination of the presence of blocking autoantibodies to FRs in serum

Efect of biological samples containing varying titers of blocking autoantibodies to FRs

METHOD FOR DETECTING THE AFFINITY OF FOLATE RECEPTOR AUTO ANTIBODIES

CROSS REFERENCE TO RELATED APPLICATION

The present application claims the benefit of priority from U.S. Provisional Application 60/424,965 filed on Nov. 8, 2002.

FIELD OF THE INVENTION

This invention relates to autoantibodies to folate receptors (FRs) on the surface of cells. In particular, the present invention relates to an assay for detecting the autoantibodies to the FRs in mammals, particularly humans. The invention also relates to the prevention of diseases, disorders or conditions associated with impaired cellular uptake of folate as a consequence of the presence of autoantibodies to the FRs, which causes folate-sensitive abnormalities, such as birth defects (e.g., a neural tube defect, i.e., NTD), infertility, spontaneous abortion, male sterility, unsuccessful in vitro fertilization, neurologic disorders, and impaired intestinal absorption of folic acid. The present invention provides a method of diagnosing such folate-sensitive abnormalities. The present invention further relates to an assay for detecting autoantibodies to the FRs in women and provides diagnostic screening for women at risk of a pregnancy with fetal complications, such as a NTD.

BACKGROUND OF THE INVENTION

Folic acid is essential for normal embryonic development because it participates in one-carbon metabolism for the synthesis of nucleic acids and amino acids required by highly proliferative embryonic cells (Lucock, *Mol. Genet. Metab.* 71:121 (2000)). Maternal nutrition, especially with regard to folate intake for the prevention of neural tube defects (NTDs), has been the focus of much attention for the past four decades. The early studies linking folate intake to the prevention of NTDs (Hibbard and Smithells, *Obstet. Gynaecol. Br. Commonwealth* 71:529 (1964); Hibbard and Smithells, *Lancet* 1, 1254(1965); Smithall et al., *Arch. Dis. Child* 51:944 (1976)) have been confirmed by recent randomized controlled studies. These studies show that women who were given periconceptional folate supplements had about a 70% reduction in the occurrence and recurrence of NTDs (Laurence et al., *Br. Med. J.* (*Clin. Res. Ed.*) 282:1509 (1981); MRC Vitamin Study Research Group, *Lancet* 338:131(1991); Czeizel and Dudas, *N. Engl. J. Med.* 327:1832 (1992)).

However, most mothers who give birth to babies having NTDs and/or other birth anomalies, do not exhibit signs of clinical folate deficiency. Therefore, extensive research has been in progress to identify genetic defects that impair cellular metabolism or uptake of folate. The effect of these genetic defects can be corrected by pharmacologic intake of folic acid (Kirke et al., *Lancet* 348:1037 (1996)). Pharmacologic intake of folic acid raises the plasma concentration of the vitamin and provides sufficient mother-to-fetus transport of folate to bypass impaired folate uptake and/or intracellular metabolism, thereby reducing the occurrence of folate-sensitive congenital abnormalities. Thus far, a number of candidate genes encoding some of the enzymes related to folate metabolic pathways have been identified in association with NTDs. These genes, however, account for only a small number of birth defects (van der Put et al., *Exp. Biol. Med.* (*Maywood*), 226:243 (2001)).

Decreased folate uptake by maternal and/or fetal placental cells and embryonic cells in the presence of normal or a low-level blood folate, may be caused by quantitative or functional defects in the membrane proteins required for the uptake of folate. No genetic abnormalities that alter expressions of these membrane proteins have been unambiguously identified (De Marco el al., *Am. J. Med. Genet.* 95:216 (2000); Barber et al., *Am. J. Med. Genet.* 76:310 (1998)).

Cellular uptake of folate is mediated via two distinct pathways: the reduced folate carrier (RFC) (Henderson, *Annu. Rev. Nutr.* 10:319 (1990)), which is an integral transmembrane protein that is present in most cells, and the folate receptor (FR), which is anchored to the plasma membrane of cells by a glycosylphosphatidylinositol (GPI) adduct that internalizes folate by endocytosis of the folate-receptor complex (Antony, *Annu. Rev. Nutr.* 16:501 (1996)). There are three isoforms of the FR ($\alpha$, $\beta$, $\gamma$), which are expressed at different levels in tissues and have different affinities to folate. Cellular uptake of folate depends on the expression levels of each folate receptor isoform (Ross et al., *Cancer* 73:2432 (1994)).

The contributions of the FRs and the RFC to the cellular uptake of folate during embryogenesis were not appreciated until Piedrahita et al. demonstrated that the ortholog of the human FR$\alpha$ in the mouse (Folbp1) is essential for embryonic organogenesis while the mouse Folbp2, which is the ortholog of the human FR$\beta$, appears to have no function in embryogenesis (Piedrahita, et al., *Nat. Genet.* 23: 228 (1999)). Nullizygous Folbp1 knockout mouse embryos (Folbp1−/−) had significant congenital malformations and none survived beyond gestation day 10, while nullizygous Folbp2−/−, heterozygous Folbp1+/− or Folbp2+/− embryos, showed no difference in development and viability as compared to wild type embryos (Piedrahita, et al.). Knockout of the RFC gene also proved lethal to embryos (Zhao, et al., *J. Biol. Chem.* 276:10224 (2001)). Heterozygous RFC dams that were given folic acid produced normal full term nullizygous RFC (−/−) offspring. These studies indicated that both RFC and FR pathways for folate uptake are essential for fetal development.

The FR$\alpha$ is expressed in human placental syncytiotrophoblasts. High concentrations of both FR$\alpha$ and FR$\beta$ isoforms are found in maternal placental tissue (Prasad et al., *Biochim. Biophys. Acta.* 1223:71 (1994)). The essential function of the FRs in human embryogenesis is to ensure cellular uptake of folate. It has been reported that mother-to-fetus transfer of folate is mediated via the FR$\alpha$ (Clark et al., *Hum. Reprod. Update* 7:501 (2001)). This prompted studies of the FR$\alpha$ gene as a candidate gene responsible for a folate sensitive birth defect, such as a neural tube defect. However, no consistent nucleotide polymorphisms or mutations that affect expression of the FR gene, or the function of the FR protein, have been identified (Barber et al.; De Marco et al.) that could account for the occurrence rate of NTDs. Instead, only a small fraction of women with a NTD-complicated pregnancy were shown to have a polymorphism in the gene encoding folate-dependent enzymes, such as methylene-tetrahydrofolate reductase (MTHFR) (Christensen et al., *Am. J. Med. Genet.* 84(2):151-57 (1999)).

Since genetic studies have not provided evidence that a mutation of relevant genes (encoding enzymes or FRs) are a significant cause of congenital dysmorphogenesis, it is, therefore, possible that NTDs and other folate-sensitive abnormalities could be autoimmune disorders. Autoantibodies to several proteins have been associated with infertility, miscarriages and fetal abnormalities (Coulam, *Early Pregnancy* 4:19 (2000); Clark et al., *Hum. Reprod. Update* 7:501

(2001)). Several previous studies demonstrated that antibodies raised in a rabbit to kidney, heart muscle, testes, placenta and other rat tissues, caused dose-dependent congenital defects and embryonic resorptions when administered to pregnant rats (Brent et al., *Proc. Soc. Exp. Bid. Med.* 106:523 (1961); Barrow and Taylor, *J. Exp. Zool.* 176:41 (1971); Brent, *Proc. Soc. Exp. Biol. Med.* 125:1024 (1967)). The mechanism by which these anomalies occurred was not established. But the administered antibodies were concentrated on the yolk sac, suggesting that the antibodies interfered with delivery of nutrients to the embryo (Slotnick and Brent, *J. Immunol.* 96:606 (1966)). Thus, it was speculated that antibodies which block the folate binding sites on the FRs (da Costa and Rothenberg, *Biochim. Biochim. Acta.* 1292:23 (1996)) could interfere with the cellular uptake of folate. Such interference would then impair intracellular folate homeostasis that is essential for normal embryogenesis and fetal development.

There is evidence that women who have had a spontaneous or induced abortion, or a later miscarriage, have an increased risk of a fetal NTD complication in a subsequent pregnancy (Evans, *Brit. Med. J.* 1: 975, (1979); Carmi et al., *Am. J. Med. Genet.* 51: 93, (1994); Cuckle, *Prenat. Diagn.* 3: 287, (1983)).

The cause of NTD(s) is multifactorial and includes chemotherapeutic drugs, especially the antifolates (Hernandez-Diaz et al., *N Engl J Med.* 343:1608-14, (2000)), anti-epileptic drugs (Dansky et al., *Neurology* 42: 32-42 (1992)) chromosomal abnormalities (Seller, *Clin Dysmorphol.* 4:202-07 (1995)), environmental (Finnell et al., *Ann NY Acad Sci.* 919:261-77 (2000)) and genetic factors (De Marco and Moroni, *Am J Med Genet.* 95: 216-23 (2000)). Studies that have shown a reduction of about 70% in the occurrence of NTDs with folic acid supplementation beginning at the time of conception (MRC Vitamin Study Research Group, supra) provide evidence that folate circumvents either an impaired intracellular folate-dependent enzymatic pathway, or an inhibitor of the cellular uptake of folate. There is, however, no evidence for diminished function of an enzymatic pathway that could account for a 70% decrease in the occurrence of NTD with the folate supplementation. It is also not known whether the folate-sensitive disorders are due to interference of folate uptake by autoantibodies to the FRs. Therefore, a woman starting a pregnancy does not know whether grain or pharmacologic folate supplements would help to prevent congenital defects, such as a neural tube defect.

The present invention relates to the discovery that folate-sensitive disorders or conditions, such as infertility, spontaneous abortion, unsuccessful in vitro fertilization, or birth defects, are due to interference of folate uptake by an autoantibody against the folate receptor. The present invention provides a reliable assay to detect autoantibodies to folate receptors in a mammal, especially in a human.

SUMMARY OF THE INVENTION

The present invention is directed to the discovery that folate-sensitive abnormalities are caused by the presence of autoantibodies to the folate receptors (FRs) in a subject's body fluids, such as serum. Such folate-sensitive abnormalities include, but are not limited to, neural tube defects (NTDs), infertility, spontaneous abortion, male sterility, unsuccessful in vitro fertilization following implantation in the uterus, neurologic disorders, e.g., dementia, or impaired intestinal absorption of folic acid.

One aspect of the present invention is directed to the identification of autoantibodies to the FRs on the surface of a cell, which blocks folate uptake and results in intracellular folate deficiency and therefore affects intracellular metabolism. Accordingly, a method for detecting the presence of autoantibodies to folate receptors in a biological sample from a subject is provided by the present invention.

Another aspect of the present invention is directed to a method for detecting the presence of blocking autoantibodies to folate receptors in a biological sample from a subject.

Still another aspect of the present invention is directed to a test kit for detecting autoantibodies to FRs in a biological sample from a subject.

Yet another aspect of the present invention is directed to a test kit for detecting blocking autoantibodies to FRs in a biological sample from a subject.

In one aspect, the present invention provides a method for diagnosing a folate-sensitive abnormality or disorder in a subject at risk of the abnormality or disorder by detecting the presence of autoantibodies to FRs in a biological sample from the subject.

In another aspect, the present invention provides a method for screening a woman at risk for having a neural tube defect-complicated pregnancy by detecting the presence of maternal autoantibodies to the FRs in a biological sample from the woman.

In still another aspect, the present invention provides a method for the prevention of folate-sensitive abnormalities or disorders.

BRIEF DESCRIPTION OF THE FIGURES

FIG. 1A: * indicates insufficient serum available for this determination. † subjects were pregnant at the time of blood sampling; ‡ Subjects 10, 11 and 12 had a NTD-complicated pregnancy and lack the autoantibody to the folate receptors. FIG. 1B: Subjects 1-4 were nulligravid, 5-16 had previous pregnancies without NTD complications, 17-24 were pregnant at the time the blood was sampled. § Serum from Control Subjects 16 and 24 contained autoantibodies to the folate receptors.

DETAILED DESCRIPTION OF TEE INVENTION

Figure 1:
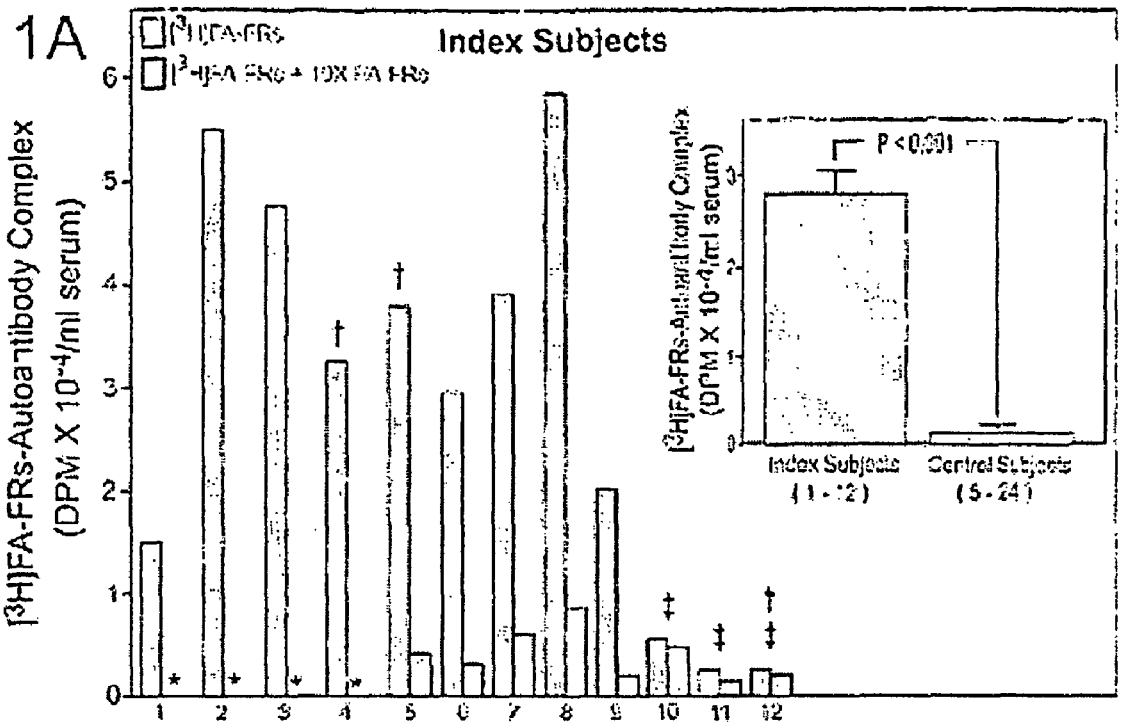
FIG. 1 Autoantibodies to Folate Receptors in the Serum from Index Subjects and Control Subjects shows the results of a binding assay for detecting autoantibodies to the FRs in serum from women with a prior NTD pregnancy or a current NTD pregnancy, and women that have no history of a NTD. Blue bars: Incubation of serum from Index and Control Subjects with [$^3$H]folic-folate receptors. Orange bars: Incubation as above with a 10 fold excess of unlabeled folic acid-folate receptors that competes out the binding of [$^3$H]folic-folate receptors to the autoantibodies. The inset depicts the mean±SEM of the values obtained for the Index and Control Subjects. Control Subjects 1-4 were nulligravid and were excluded from the statistical analysis for the lack of a recognized pregnancy. The P-value was determined using Student t-test.
Figure 1:
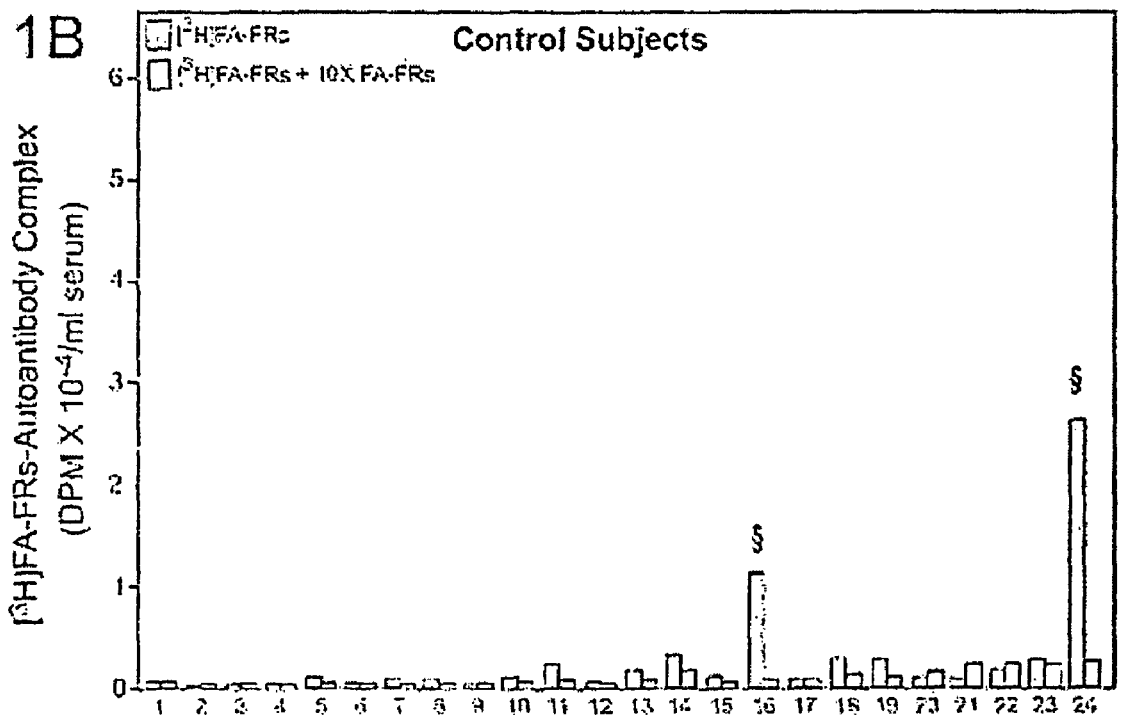

The present invention is directed to the discovery that folate-sensitive abnormalities, such as neural tube defects (NTDs), infertility, spontaneous abortion, unsuccessful in vitro fertilization, neurologic disorders (e.g., dementia), or impaired intestinal folate absorption, are caused by the presence of the autoantibodies to the folate receptors (FRs) in a subject's body fluids, such as serum.

By "test group" or "index group" is meant a group of women, each of whom had a previous pregnancy, or is currently enduring a pregnancy complicated by abnormal fetal development of the central nervous system; or previously gave birth to a baby having congenital abnormalities. By "control group" is meant women who previously had normal pregnancies; women who have never given birth to a baby having a NTD; women who have never been pregnant (nulligravidas); or women who have never given birth previously (nulliparous).

By "diagnosing", "diagnosis", "detecting" or "screening" is meant an act or process of identifying or determining the presence, nature and cause of a folate-sensitive abnormality or disorder, through evaluation of patient history, examination and identification of the presence, in the serum or other body fluids of a subject, of autoantibodies against the folate receptors.

By "subject" is meant any mammalian subject, such as a human. A preferred subject is a woman who previously gave birth to an infant having a NTD, a woman who was pregnant with a conceptus having a NTD, a woman who had a spontaneous or induced abortion, or a later miscarriage. Another preferred subject is an egg-donor (i.e., female) or a sperm-donor (i.e., male) for an in vitro fertilization procedure. By "index subject" is meant a subject in an index group or test group.

By "control subject" is meant a subject in a control group. Without intending to be bound by any particular theory, it is believed that women who had an induced abortion or a miscarriage may have developed autoantibodies to the FRs but not any of the folate-sensitive developmental abnormalities. Therefore, such women are also considered as control subjects in the present invention.

By "risk" is meant the frequency or possibility of contracting, developing or having a folate-sensitive abnormality or disorder, such as infertility, spontaneous abortion, unsuccessful in vitro fertilization following implantation in the uterus, neurologic disorders (e.g., dementia), or impaired intestinal folate absorption. "Risk" in accordance with the present invention also connotes giving birth to a baby having congenital birth defects, such as NTDs, or enduring a pregnancy with a conceptus having congenital birth defects.

By "prevention" or "prevent" is meant that the risk of having an abnormality or disorder can be predicted or determined in sufficient time so as to keep the disorder or abnormality from occurring or significantly reduce the risk of having the abnormality or disorder.

By "biological sample" is meant a clinical sample for testing taken from any tissue of a mammal, preferably, body fluid from a mammal, more preferably, serum from a human. By "control sample" is meant a biological sample taken from a subject that is the same or homologous species as the subject to be assayed for autoantibodies and is known to have normal biological state, e.g., without detectable autoantibodies against folate receptors. A control sample includes a sample taken from a control subject.

An "antibody" refers to an immunoglobulin of any class or subclass, a portion thereof or an active fragment thereof, wherein an active fragment of an antibody retains its specific binding capability. As used herein, an "autoantibody" refers to an antibody, e.g., an IgG antibody, in a subject that is directed against components of the subject's own body. An "autoimmune disorder" refers to a disorder or condition that a subject's immune system mistakenly attacks and leads to the destruction of the subject's own body cells and/or tissues. An "autoantibody to the folate receptors (FRs)" refers to any autoantibody that is directed against any isoform or peptide sequence of the FRs, including the α and β isoforms of the FRs. In the present invention, autoantibodies against FR(s) are also termed anti-FRs auto antibodies.

The "cell membrane folate receptors (FRs)" or "cell surface folate receptors (FRs)" refers to any folate receptors (FRs) on the surface/membrane of a cell; "circulating folate receptors (FRs)" refers to any isoform of a folate receptor or its antigenic component(s) that circulates in the body fluid of a subject. By "apo-FRs" is meant any folate receptor without the ligand, i.e., folic acid, bound to it.

By "folate binding capacity" used herein is meant quantified amount of the folic acid bound to the FRs on the membrane or matrix per unit volume, e.g., per milliliter, of the membrane or matrix.

By "cell" used herein can be any cell of a tissue culture cell line or any cell within a specific tissue/organ that binds and internalizes folate, e.g., the granulosa cells that surround the ovum in the ovarian follicle of a mammal, the epithelial cells lining the oviduct of a mammal (i.e., fallopian tubes in humans), cells of the endometrial lining of a mammalian uterus, cells of the mammalian placenta, the cells of choroid plexus of a mammalian brain, the cells of intestinal mucosa of a mammal, or any mammalian cultured cell line, e.g., KB cells.

A "blocking autoantibody" refers to an autoantibody that binds with its antigenic component(s) and blocks the function of the antigen, which in this instance, blocks folate binding to the cell membrane FRs and the subsequent folate uptake by the cells.

By "folate supplement" is meant folic acid or folinic acid administered to a subject in order to overcome intracellular folate deficiency, particularly because of blockage of the folate uptake mechanism by autoantibodies to folate receptors. By "pharmacologic amount" is meant an amount much greater than normal to overcome the deficiency or disorder, e.g., a pharmacologic amount of folate supplement in the present invention can be referred to at least 0.8 mg of folic acid daily but not more than 4 mg daily to an adult woman.

"Label," "labeled" or "detectably labeled" refers to incorporation of a detectable marker, for example, by incorporation of a radioactively labeled compound or moieties attached to a compound or polypeptide, such as biotin, which can be detected by the binding of a second moiety, such as labeled avidin. Various methods of labeling polypeptide, nucleic acids, carbohydrates, and other biological or organic molecules are known in the art. Such labels can have a variety of readouts, such as radioactivity, fluorescence, color, chemiluminescence or other readouts known in the art or later developed. The readouts can be based on enzymatic activity, such as beta-galactosidase, beta-lactamase, horseradish peroxidase, alkaline phosphatase, luciferase; radioisotopes such as $^3H$, $^{14}C$, $^{35}S$, $^{125}I$ or $^{131}I$); fluorescent proteins, such as green fluorescent proteins (GFP); or other fluorescent labels, such as FITC, rhodamine, and lanthanides. Where appropriate, these labels can be the product of the expression of reporter genes, as that term is understood in the art.

"Treating" or "treatment" as used herein means to ameliorate, suppress, mitigate or eliminate the clinical symptoms after the onset (i.e., clinical manifestation) of a disease state. An effective or successful treatment provides a clinically observable improvement.

A "specific binding member" refers to a member of a group of two or more moieties that can specifically bind with each other rather than becoming non-specifically associated with each other, such as by precipitation. Examples of specific binding members include, but are not limited to, antigen-antibody, receptor-ligand and nucleic acid-nucleic acid pairs.

"Specific," "specifically," "specifically bind" or a "specific binding reaction" in the context of the binding of a first specific binding member with at least one other specific binding member refers to binding that is preferential and not non-specific. Preferably, a specific binding reaction is unique for the specific binding members, but that need not be the case.

"Detectably bind" refers to the specific binding of one specific binding member with at least one other specific binding member that can be detected. For example, one specific binding member can be detectably labeled such that the detectable presence of the label indicates a specific binding event. The detection limits of such detectable binding are related to the detectable label used and the detection method or device used. "Detectably label" refers to detectably binding of a label.

A "tissue" refers to a collection of cells as known in the art. A "culture" of cells is a collection of cells as known in the art and can be a clonal population of cells or a mixed population of cells.

A "sample" includes any physical sample that includes a cell or a cell extract from a cell, a tissue, a biopsy sample, a tissue extract, for example. A sample can be from a biological source such as a subject or animal or a portion thereof, or from a cell culture. Samples from a biological source can be from a normal or abnormal organism (such as an organism suffering from a condition or disease state, such as a NTD) or portion thereof and can be from any fluid, tissue or organ, including healthy or abnormal (such as diseased) body fluids, tissues or organs.

The present invention is directed to the identification of autoantibodies to folate receptors (FRs) on the surface of a cell, or any FRs isoform thereof, in a biological sample from a subject, e.g., serum of a woman. Without intending to be bound to a particular mechanism, it is believed that the autoantibody blocks folate uptake and results in intracellular folate deficiency and therefore affects intracellular metabolism.

One embodiment of the present invention is directed to a method for detecting the presence of autoantibodies to folate receptors (FRs) or anti-FRs autoantibodies in a biological sample of a subject comprising:
   a. acidifying the biological sample to a pH about 3.0 to pH about 5.0, preferably pH about 3.5, whereby the anti-FRs autoantibodies and endogenous folate are dissociated from the endogenous FRs, which are in circulation following their release from cell membranes in vivo, under an acidic condition so that apo-FRs in the biological sample are generated, b. removing the dissociated endogenous folate, preferably, by adsorption of the dissociated folate to dextran or hemoglobin-coated charcoal,
c. subsequent incubating the biological sample with labeled folic acid (FA) at a pH about 8.0 to pH about 8.9, preferably pH about 8.6, to permit the formation of labeled FRs by the binding of the labeled FA to the apo-FRs under the basic pH condition present in the biological sample,
d. incubating the biological sample from Step c with labeled purified FRs, whereby these additional FRs are added to the biological sample because the endogenous FRs concentration may be low and thereby not sufficient to detect all the autoantibodies and whereby at the basic pH, the autoantibodies that dissociated from the endogenous FRs in Step a bind to either the low concentration of labeled endogenous FRs, i.e., labeled FRs from Step c, or to the additional labeled purified FRs, and
e. detecting and quantifying the formation of an immune complex between the anti-FR autoantibodies present in the biological sample and the labeled FR, either purified or endogenous FRs, whereby the immune complexes can be separated for detection and quantification by precipitating the immune complex by ammonium sulfate, sodium sulfate, alcohol, or polyethylene glycol with the addition of carrier IgG, or by adding, incubating and precipitating with an immunoglobulin-binding agent, e.g., an anti-IgG and/or anti-IgM antibody which can also be detectably labeled, preferably, by adding to the reaction with a protein-A membrane suspension, e.g., a *Staphylococcus* protein-A membrane suspension, incubating at a low temperature for a period of time sufficient to bind all the IgG (including the autoantibodies in the form of antoantibody-FRs immune complex) to the protein A membrane, e.g., at 4° C. for 10 minutes, and whereby the presence of the immune complex is indicative that the subject has anti-FRs autoantibodies.

According to the present invention, an example of the above method comprises following steps:
a. acidify the biological sample of a subject to an acidic pH, preferably, to about pH 3.5,
b. remove dissociated folate from the acidified sample, e.g., by adding dextran-coated charcoal to adsorb the dissociated folate in the acidified sample,
c. purify solubilized FRs, preferably non-aggregated or monomeric FRs, from cell membranes of a mammal which is the same species as the subject; and dissociate the endogenous folate bound to the solublilized FRs protein by acid treatment of the sample, followed by charcoal treatment, raising the pH to 7.4, followed by the binding of the resulting apo-FRs to a folic acid affinity matrix. The resulting purified FRs are eluted from the affinity matrix at an acidic pH, preferably pH 3.5, and the neutralized to pH about 7.4.
d. incubate the purified FRs from Step c with folic acid (FA) which is labeled in some way that can be visualized or detected by an assay, e.g., labeled with radioactive [$^3$H], in a neutral pH, preferably, pH 7.4, to generate the labeled FA-FRs antigen complex, e.g., [$^3$H]FA-FRs. A sufficiently labeled FRs, e.g., 10-20% excess labeled FA over the concentration of the FRs, is added so that all purified FRs in the solution are coupled with at least one labeled FA and there is free or unbound excess labeled FA in the solution,
e. adjust the solution from Step d to a basic pH, preferably, to pH 8.9, more preferably, with 0.2 M veronal at pH 8.9,
f. divide solution of Step e equally into a first test tube and a second test tube, and add a 10 to 20 fold greater concentration of unlabeled FA-FRs to the second test tube,
g. add an equal volume of the sample from Step b to the first and second tubes of Step f, and incubate the mixture for a sufficient time at a low temperature, e.g., for 24 hours at 4° C., so that the autoantibodies to the FRs from the biological sample bind preferentially to the higher concentration of the labeled FA-FRs than to lower concentration of the soluble FRs in the biological sample. If the binding of the labeled FA-FRs to the autoantibody is specific, this binding is competed out by the excess unlabeled FA-FRs contained in the second tube,
h. separate the resulting labeled FA-FRs from labeled FA-FRs-autoantibody complex after the incubation in Step g, e.g., by adding to the reaction a protein-A membrane suspension, preferably, a *Staphylococcus* protein-A membrane suspension, and incubating at a low temperature for a period of time sufficient to bind all the IgG to the protein A membrane, e.g., at 4° C. for 10 minutes, or, alternatively, by adding an anti-IgG or IgM antibody, e.g., an antibody raised in a rabbit or goat to the human IgG (or IgM) in ammonium sulfate, sodium sulfate, 50% ethanol, polyethylene glycol,
i. centrifuge the resulting products of step h at a speed and for a period of time, e.g., at 6000 RPM for 3 min, sufficient to precipitate the labeled FA-FRs-autoantibody complex in step h, e.g. the complex bound by the protein A or the anti-IgG (or IgM) antibody,
j. remove the supernatant fraction and wash the pellets 3 times with a washing solution, e.g., 0.01 M sodium phosphate buffer, pH 7.4, containing 0.05% Triton X-100,
k. suspend the washed pellet in scintillation cocktail and determine the radioactivity present using a scintillation counter,
l. compare the quantity of the label present in the pellets from the first test tube and the second test tube. If the label, e.g., the radioactivity, of the pellet from the first test tube is significantly greater than the label of the pellet from the second test tube, it indicates that the biological sample being tested contains the autoantibodies to the FRs. A quantitative estimate of the autoantibody titer is determined by the amount of labeled receptor bound. This would be the molar equivalent of the labeled FA bound to the FRs by the methods described in Example 2.

Another embodiment of the present invention is directed to a method for detecting the presence of an autoantibody that blocks the binding of folate to FRs, i.e., a blocking autoantibody, in a biological sample from a subject comprising:
a. obtaining a FRs-bound matrix, e.g., preparing placental membranes by homogenizing human placenta in three volumes of buffer, pelleting the membranes by centrifugation, followed by three washes in the same buffer,
b. dissociating folatate bound to the FRs on the matrix by acidifying said matrix at a pH about 3.0 to pH about 5.0, preferably, pH about 3.5, to generate the apo-FRs on the matrix,
c. removing the dissociated folate from Step b, e.g., by washing the matrix in an acid buffer,
d. resuspending the matrix at a pH about 7.0 to pH about 8.6, preferably, pH about 8.6,
e. determining the folate binding capacity per unit volume, e.g., by adding to a portion of the matrix an amount of labeled folic acid, washing to removing free labeled acid, and quantifying the amount of the folic acid bound to the FRs on the matrix per unit volume, e.g., per milliliter, of the matrix, f. removing free folate from the biological sample, e.g., by acidifying the biological sample and treating the acidified biological sample with dextran or hemoglobin-coated charcoal, g. obtaining a control sample, whereby free folate in the control sample is removed by acidifying the control sample and treating the control sample with dextran or hemoglobin-coated charcoal, h. incubating suspended matrix from Step d with said biological sample from Step f, in a buffer of pH about 8.6, i. incubating suspended matrix from Step d and with said control sample from Step g, in a buffer of pH about 8.6, j. washing said matrix from Step h and Step i, e.g., with cold buffer and determining the folic acid binding capacity of the membrane suspension for both biological samples, k. incubating said matrix from Step j with labeled folic acid, l. determining and quantifying the labeled folic acid binding capacity of the matrix from Step h and to the matrix from Step i, whereby a reduction of the labeled folic acid binding to the matrix in Step h when compared to the labeled folic acid binding to said matrix from Step i indicates the presence of autoantibodies that block the binding of folate to FRs in the subject.

In a preferred embodiment, the FRs in the present invention are detectably labeled, as describe above.

According to the present invention, the method for identifying the autoantibodies to the FRs employs purified FRs, preferably non-aggregated or monomeric FRs, e.g., prepared from the membrane proteins isolated from mammalian placenta, such as human placenta. See e.g., Example 2. The solubilized placental FRs serve as the reagent antigens after dissociating the endogenous folate and purifying the FRs by coupling endogenous folic acid to a matrix, such as Sepharose 6B (Sadasivan et al., *Biochim. Bioph. Acta.* 925:36-47 (1987)). The FRs are eluted from the matrix at an acidic pH, preferably pH 3.5, and neutralized to pH about 7.4. The prepared FRs can be used either in a radioactive assay or a non-radioactive assay, such as ELISA.

In accordance, a particular embodiment of the present invention is directed to a method for identification of autoantibodies to the folate receptors (FRs) in a subject's body fluids, e.g., serum of a woman by ELISA assay. The contemplated method comprises coating the wells of the ELISA plates with purified folate receptor protein from Step c above; adding treated sample prepared as described in Step a-b above to the neutralizing buffer contained in the well; after an incubation period, washing the wells with neutral buffer and then adding a secondary biotinylated anti-human IgG antibody to the wells; after an incubation period, washing the wells again with the same washing buffer and then adding the avidin-biotin-alkaline phosphatase (or peroxidase) complex; and after an additional incubation, adding the chromogenic substrate (p-nitrophenyl-phosphate); the intensity of the color developed is quantified by reading the absorbance at 405-420 nm in the microtitration plate reader. This technique can also be used to assay for IgM autoantibodies to the folate receptors utilizing a secondary biotinylated anti-human IgM antibody.

In another particular embodiment, the present invention is directed to a method for identification of autoantibodies to the folate receptors (FRs) in serum of a woman by the binding of radiolabeled FRs. According to the present invention, the serum from subjects to be tested for the autoantibodies is acidified with an acid or acidic reagent to adjust the pH of the serum to about 3.5. Examples of such acid or acidic reagents include glycine-HCl or any other acid buffer. At the acidic pH, soluble FRs in the serum are dissociated from the circulating autoantibodies. The acidic pH also dissociates endogenous folate from any serum receptor. The dissociated folate is then removed from the serum by techniques known to skilled artisans, such as by adding dextran-coated charcoal to bind the dissociated folate. The acidified serum is mixed with [$^3$H]FA-FRs, which consists of purified FRs, prepared as described above with an excess amount, preferably about 10-20%, more preferably about 20%, of radioactive labeled folic acid ([$^3$H]FA). The [$^3$H]FA-FRs are in a solution at a basic pH before being mixed with serum, preferably in a solution at a pH of about 8.9. More preferably, the [$^3$H]FA-FRs are in a 0.2 M veronal solution at a pH of about 8.9. When the prepared FRs and the acidified serum are mixed, the resulting pH is 8.6 and the autoantibodies to the FRs in the subject's serum bind preferentially to the higher concentration of the radiolabeled FRs than to the lower concentration of the soluble FRs in the serum. The autoantibody-FRs immune complex is adsorbed to *Staphylococcus* protein A membranes. The membranes are washed 3 times and then suspended in the scintillation cocktail. The radioactivity is detected in a scintillation counter. The radioactivity in the assayed sample is compared to the radioactivity in a control (the second test tube as described above), which contains [$^3$H]FA-FRs complex with an excess of unlabelled FA-FRs complex. The unlabelled FA-FRs complex in the control sample is preferably at least at a concentration greater than 10 times of that of the [$^3$H]FA-FR complex. If there are no autoantibodies to the FRs in the serum, the protein A in both of the first and second test tubes will only bind to other non-autoantibody-to-FR IgGs or antibodies in the serum. The non-autoantibody-to-FRs, IgGs or antibodies will not be labeled specifically with [$^3$H]FA-FRs and thereby [$^3$H]FA-FRs will be washed away. Accordingly, no radioactivity can be detected in either the first or the second test tube. If there are autoantibodies to the FRs in the serum, the protein A in the first test tube will bind these autoantibodies specifically and such autoantibodies will still bind to the protein A after washing, while the [$^3$H]FA-FRs in the form of autoantibody-[$^3$H]FA-FRs complex in the second test tube will be competed out by the excessive amount of unlabeled FA-FRs. Accordingly, the pellet in the second tube will be protein A bound with autoantibody-FA-FRs and therefore a very low base level radioactivity is detected. Therefore, if the radioactivity from the protein A membrane from the test sample (the first test tube) is greater, preferably five times greater or more, than the radioactivity from the protein A membrane of the control sample (the second test tube), it is concluded that autoantibodies to FRs are present in the subject. The presence of autoantibodies to FRs indicates that the subject is at risk of a pregnancy with fetal complications or at risk of folate-sensitive abnormalities, e.g., giving birth to a baby with congenital birth defects, such as NTDs. An example of the assay methodology using the radioactive labeled-FRs is illustrated in Example 3 below.

Still another embodiment of the present invention is directed to a test kit for detecting autoantibodies to FRs in a biological sample from a subject comprising purified FRs from a human or homologous species, preferably non-aggregated FRs, reagents for treating (e.g. acidifying) the biological samples from subjects, labeled folic acid, and at least one indicator which detects a complex of the purified FRs and anti-FR(s) autoantibodies. A positive result indicates the presence of the autoantibody to the FRs in a subject, thereby establishing an increased risk for the subject having infertility, spontaneous abortion, male sterility, unsuccessful in vitro fertilization procedure, neurologic disorders, or impaired absorption of folic acid, or having a pregnancy with fetal complications, such as NTDs.

By "test kit" is meant a package for commercial sale, containing materials needed for an assay.

Figure 9A:
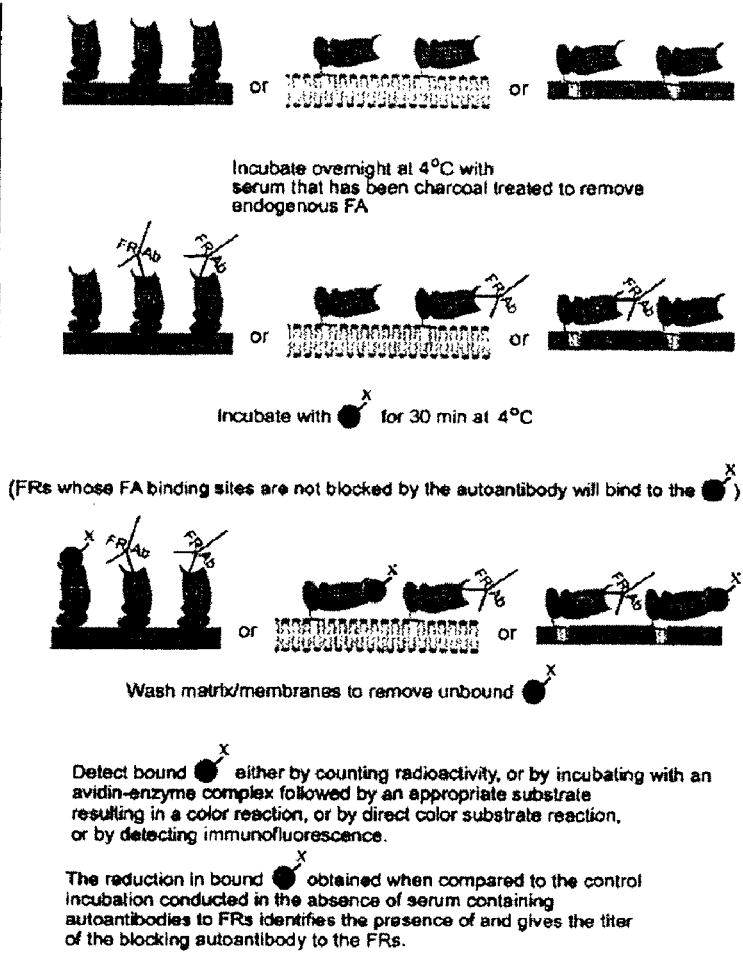
FIG. 9 shows the principles and the methodology for detecting the presence of blocking autoantibodies in the serum to the FRs.
Figure 9B:
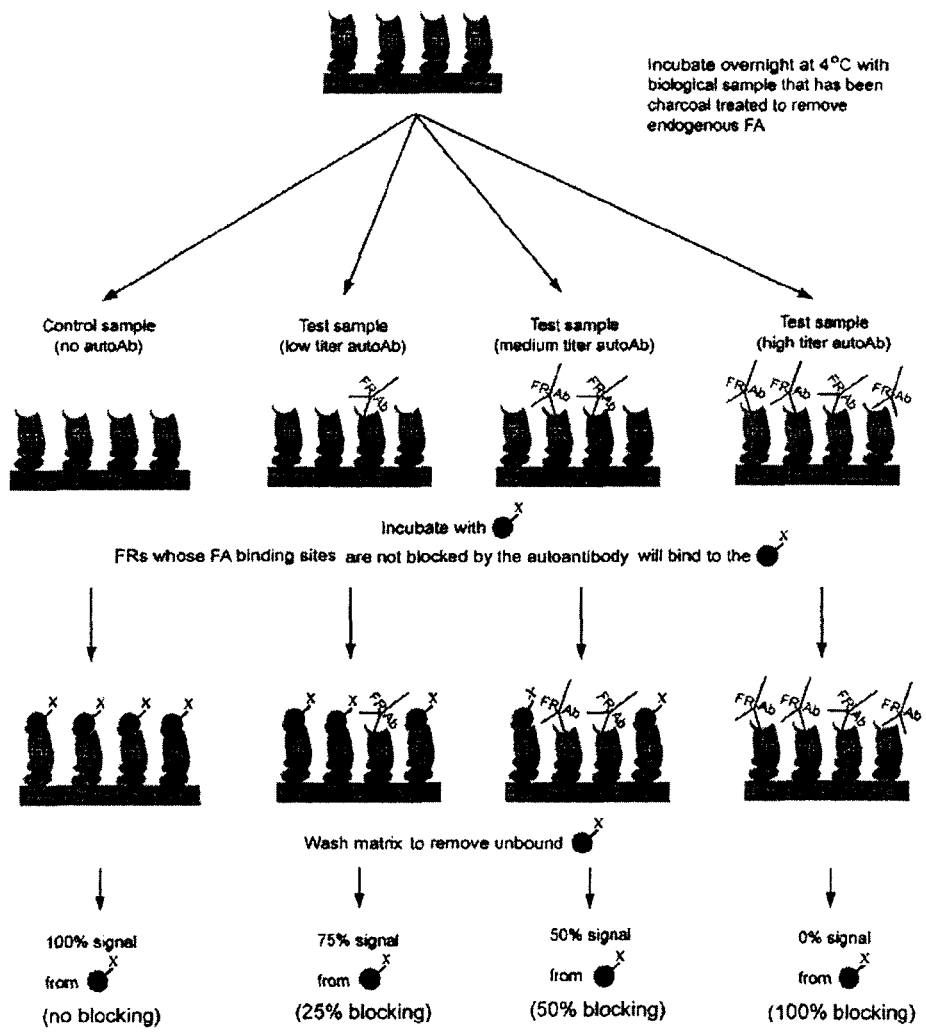

Yet another embodiment of the present invention is directed to a test kit for detecting autoantibodies to FRs that block the binding of folate by the FRs in a biological sample from a subject comprising apo-FRs from a human or homologous species, reagents for treating the biological samples from subjects, labeled folic acid, and at least one indicator which detects the apo-FRs remaining in the reaction. The contemplated components and principles of the methodology of this test kit is illustrated in FIG. 9. The apo-FRs can be purified glycosylphosphatidylinositol (GPI)-FRs bound to a matrix (membrane, or via hydrocarbon chain or other hydrophobic matrix, such as human placental membrane) or FRs covalently coupled to a matrix. Labeled folic acid (FA) refers to FA coupled to a carrier, e.g., enzyme or radioactive label, or fluorescent marker, or biotin. The reduction in bound FAs obtained, which are coupled to a carrier, compared to the control incubation which is conducted in the absence of the biological sample to be tested or in the presence of a control sample indicates the presence of blocking autoantibodies to the FRs and provides the titer of the blocking autoantibodies to the FRs. See FIG. 9A and FIG. 9B.

Accordingly, the test kits the present invention provided herein can also determine the titer of blocking autoantibodies. The test kits of the present invention can be also employed to determine the apparent association constant (Ka) of the blocking autoantibodies to said FRs.

According to the present invention, the biologic effect of the autoantibodies to the FRs on the cellular uptake of folate is a function of two parameters: the titer of the autoantibodies in the body fluids, and the affinity (i.e., association constant, Ka) of the autoantibody for binding to the FRs on the cell membranes. If the autoantibodies have a high affinity constant ($K_a$ of $10^9$ to $10^{10}$ L/mole) and the titer of the autoantibodies is high (i.e., sufficient to bind to all the FRs), this will block the cellular uptake of folate resulting in intracellular folate deficiency. In order to prevent the action of this antibody scenario, one has to administer a very large amount of pharmacologic folic acid. If the apparent $K_a$ for the binding of the autoantibodies to the FRs is lower (e.g., $10^6$-$10^7$ L/mol), even if the titer is sufficient to bind to all the FRs on the cell membranes, a much lower concentration of folate may be sufficient to compete with the autoantibodies for binding to the FRs and therefore prevent intracellular folate deficiency. Thus, the different combinations of autoantibody titer and the apparent $K_a$ of the autoantibodies for binding to the FRs can be predictive of the biologic effect of the autoantibodies on intracellular folate metabolism. A third factor can also occur: If there is a very high titer of the autoantibodies there can be an acute immunological reaction that can cause tissue damage without folate deficiency.

In a particular embodiment of the present invention, the FRs in the test kits are bound to a matrix, preferably a hydrophobic matrix, more preferably placental membrane containing FRs from a human or homologous species.

According to the present invention, the indicator in the test kits is selected from the group consisting of enzyme, radioactive label, fluorescent marker, or biotin complexed with avidin.

In one embodiment, the present invention is directed to a method for diagnosing a folate-sensitive abnormality or disorder in a subject at risk of the abnormality or disorder comprising the detection of the presence of autoantibodies to FRs in a biological sample according to the methods described above.

In another embodiment, the present invention is directed to a method for screening a woman at risk for having a neural tube defect-complicated pregnancy comprising, detecting the presence of maternal autoantibodies to the FRs in a biological sample from a woman according to the methods described above. The method comprises identification of autoantibodies to the FRs in the woman's serum using the methods described above, e.g., either by radioactivity assay or by ELISA assay. The detection or identification of autoantibodies to FRs can be used to avoid the risk of having a pregnancy with fetal complications or the risk of giving birth to a baby having congenital abnormalities, such as NTDs.

According to the present invention, the cause of folate-sensitive congenital central nervous system defects, such as NTDs, has been identified. Specifically, the inventors have discovered that maternal autoantibodies to the FRs increase the likelihood for giving birth to an infant having a central nervous system defect, such as a NTD.

For example, in accordance with the present invention, the serum from a woman, who either previously gave birth to an infant having a central nervous system defect or was pregnant with a fetus having a NTD; or had a spontaneous or induced abortion, or a later miscarriage, can be analyzed for autoantibodies to the FRs, using an assay as described above. According to the present invention, identification of autoantibodies to the FRs indicates that the woman should receive a prescription for folic acid or folinic acid prior to the start of the next pregnancy to assure that the intake of the vitamin occurs at the time of conception.

According to the present invention, the inventors have discovered that an antiserum to the FRs in the rat can induce embryonic and fetal abnormalities. According to the present invention, it has been discovered that folate-sensitive congenital central nervous system defects, such as NTD, in embryos, result from autoimmune disorders. Without intending to be bound by a specific mechanism, folate-sensitive congenital abnormalities are caused by autoantibodies to the mother's folate receptors on the reproductive tissue and on the embryo that interfere with the cellular folate uptake and thus affect maternal-to-fetal transport of folate necessary for normal embryogenesis.

According to the present invention, an assay or a method as described in the present invention for identification or detection of autoantibodies to folate receptors in the serum of a subject provides a strong indication of the risk a woman has for giving birth to an infant having a teratogenic abnormality, for example, a NTD. The subject can be any mammalian subject, particularly a human, more particularly, a woman who either previously gave birth to an infant having a NTD or was pregnant with a fetus having a NTD; or a woman who had a spontaneous or induced abortion, or a later miscarriage. The biological sample to be assayed is serum or plasma. Without wishing to be bound by a particular mechanism, it is believed that the autoantibodies detected in the present invention interfere or block the binding of folate to its receptor, thereby inhibiting the uptake of folate by the early embryo. As a consequence, the inhibition leads to a NTD, or other folate-sensitive congenital birth defects.

In accordance, by examining the serum, using an assay or method as described above, for autoantibodies to the FRs in women who had either a previous or current pregnancy complicated by abnormal development of the central nervous system, or women who gave birth to a baby having congenital abnormalities, such as NTDs, the inventors have identified such autoantibodies to the FRs in women who gave birth to infants with a spinal cord abnormality. For example, in one assay, the serum from 9 (Subject #1-9 in FIG. 1) out of 12 women (75%) of a test group had the autoantibody to the FRs in their serum. The group consisted of 12 women, each of whom either had a previous or was undergoing a pregnancy complicated by abnormal development of the central nervous system. In contrast, only 2 women (Subject #16 and 24 in FIG. 1) in the control group had autoantibodies to the FRs in their serum, but did not have a NTD complicated pregnancy.

Another embodiment of the present invention provides methods for detection of the autoantibodies to FRs, which can be useful in diagnosing infertility, spontaneous abortion, unsuccessful in vitro fertilization, neurologic disorders (e.g., dementia) or impaired intestinal folate absorption, particularly due to abnormal metabolism or uptake of folate, in a mammal subject, preferably in a human subject.

In a particular embodiment, the present invention is directed to a method of diagnosing a subject having a risk of infertility, spontaneous abortion or male sterility, by detecting in serum of the subject the autoantibodies to the FRs.

Figure 2:
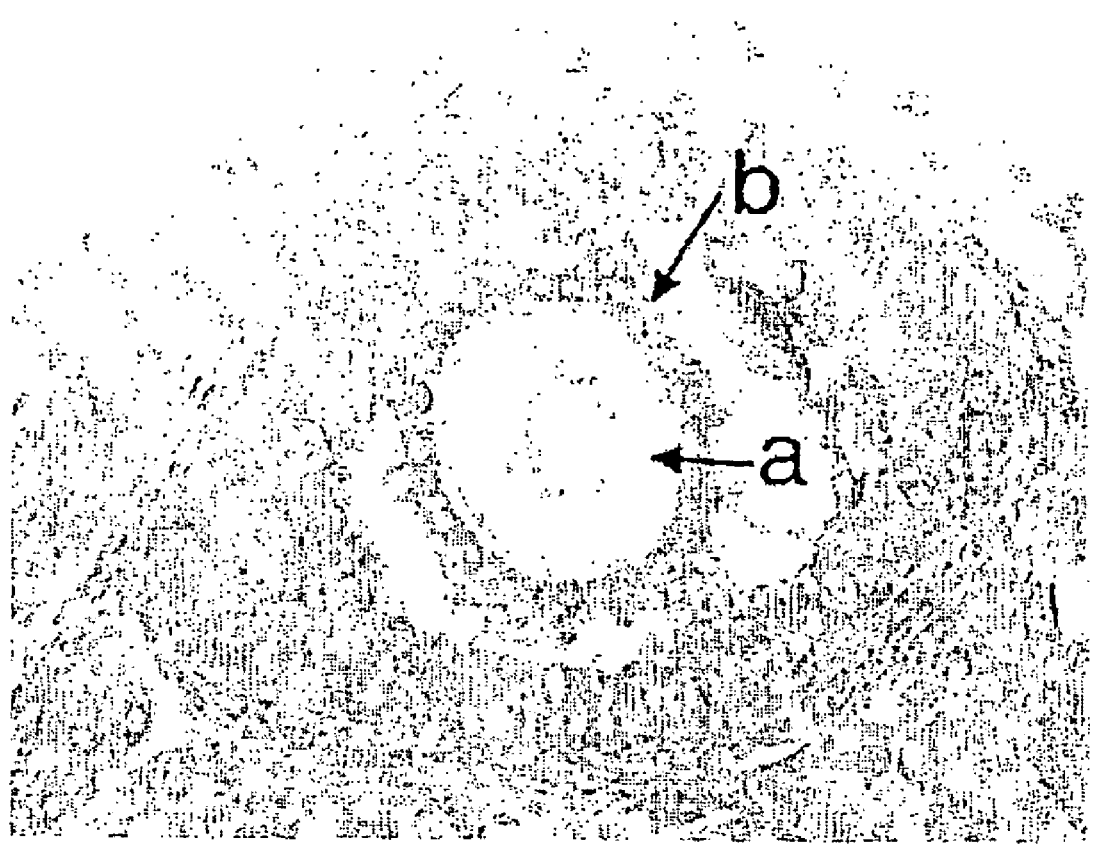
FIG. 2 Ovarian follicle from a rat showing expression of the FRs on the oocyte and the granulosa cells: shows that FRs are expressed on the granulosa cells that surround the ovum in the ovarian follicle of a rat. Antibodies to the rat FRs (purified from rat placenta) were produced in a rabbit, and used to localize the FRs present on the ovary of a rat. The brown/orange color identifies the FRs. Oocyte, a; granulosa cells, b.
Figure 3:
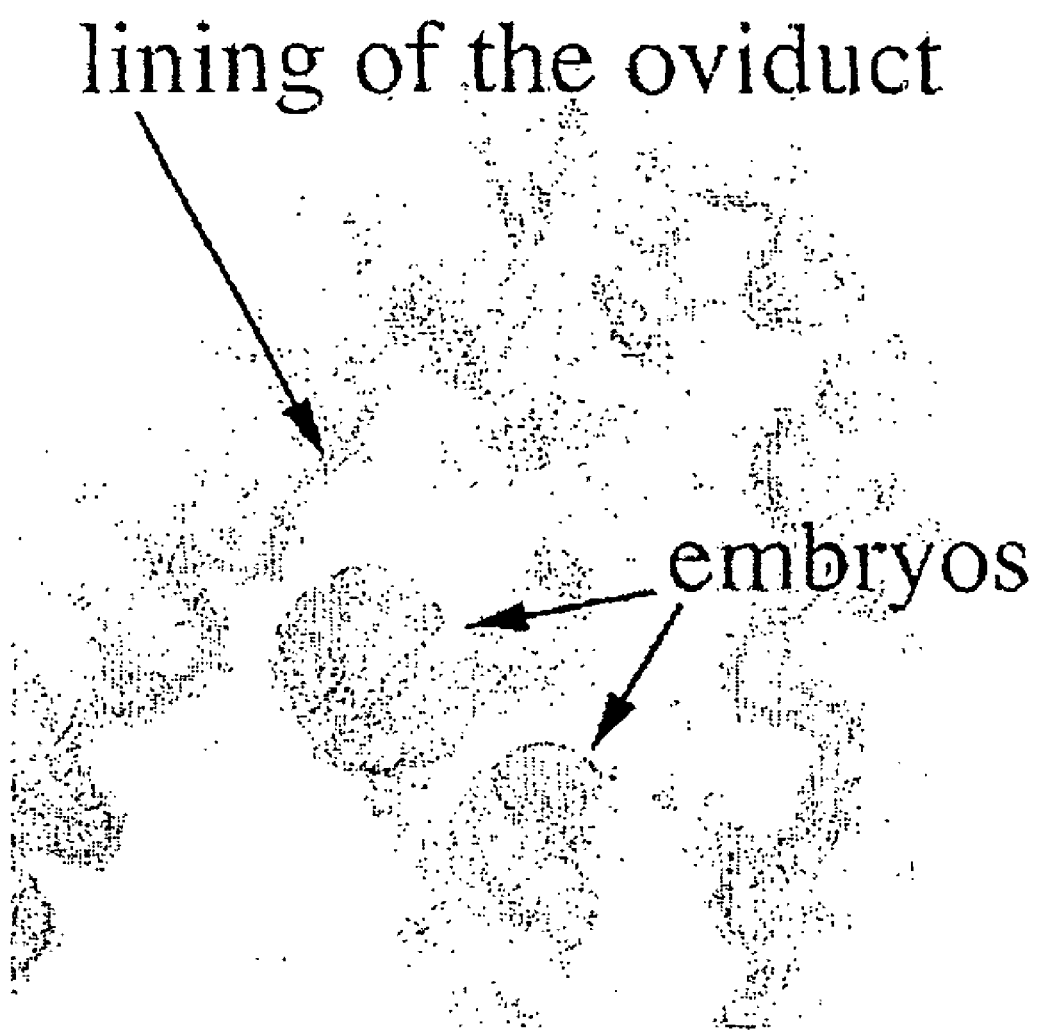
FIG. 3 The Oviduct of a rat (fallopian tube in a human) showing expression of the FRs on the epithelial lining and on two embryos: shows that epithelial cells lining the oviduct of a rat (fallopian tubes in human beings) express the FRs to which the autoantibodies can bind, thereby interfering with the advancement of the fertilized ovum (that has progressed to a blastocyst stage) to the uterus The autoantibodies can block the uptake of folate by the epithelial cells and this contributes to infertility by interfering with the intracellular metabolism that requires folate. Antibodies to the FRs present on reproductive tissue of the rat. The brown/orange color identifies the FRs.

According to the present invention, FRs are expressed on the granulosa cells that surround the ovum in the ovarian follicle of a mammal, such as a rat or a human (FIG. 2). The binding of autoantibodies to the FRs on the granulosa cells impedes the release of the mature ovum into the oviduct (i.e., Fallopian tubes) and interferes with fertilization. The autoantibodies to the FRs can also prevent fertilization of the ovum by sperm reaching the ampullae of the fallopian tubes and thereby resulting in infertility. According to the present invention, the epithelial cells lining the fallopian tubes also express the FRs (FIG. 3) to which the autoantibodies to the FRs can bind, thereby interfering with the advancement of the fertilized ovum (that has progressed to a blastocyst stage) that is entering the uterus. The autoantibodies to FRs can also block the uptake of folate by the epithelial cells and thereby contribute to infertility by interfering with the function of the fallopian tubes. Localization of the FRs on human fallopian tubes has been shown by Weitman et al. *Cancer Res* 52:6708 (1992).

Figure 4:
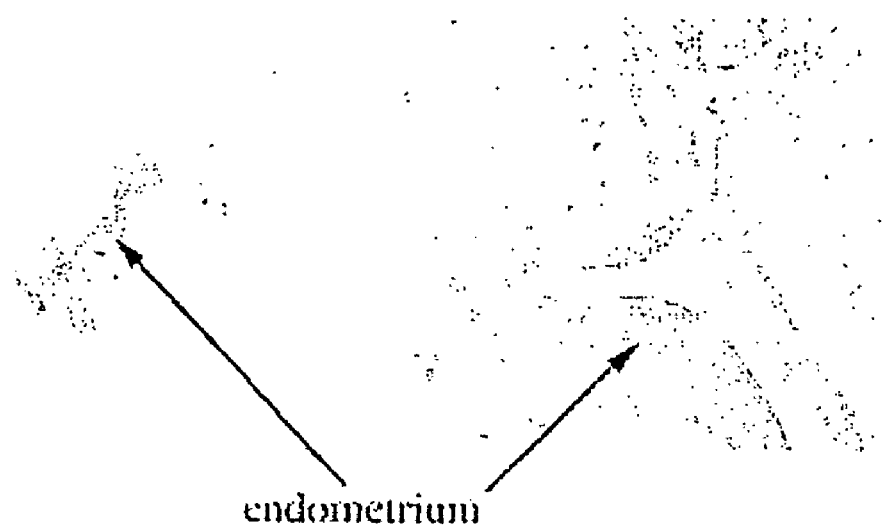
FIG. 4 The uterus of a rat showing expression of the FRs on the endometrial lining: shows that the folate receptors are highly expressed on the endometrial lining of a rat uterus. Antibodies to the rat FRs (purified from rat placenta) were produced in a rabbit, and used to localize the FRs present on the endometrium of the uterus of the rat. The brown/orange color identifies the FRs.

According to the present invention, the folate receptors are also expressed on the epithelial lining of the rat uterus (FIG. 4). Similar expression of the FRs has been shown on human endometrial tissue (Weitman et al.). The autoantibodies to the FRs can bind to these folate receptors thereby blocking folate uptake by these cells. The resulting folate deficiency can impair implantation of the blastocyst thus resulting in infertility or spontaneous abortion.

Figure 5:
FIG. 5 FRs expression on the epididymis of a rat: shows that the folate receptors are highly expressed on the epithelial cells of the epididymis of a rat. Antibodies to the rat FRs purified from rat placenta were produced in a rabbit, and used to localize the FRs present on the epididymis of a rat. The brown/orange color identifies the FRs.

According to the present invention, the folate receptors are also expressed on the epithelial cells of the epididymis of the rat (FIG. 5), and on rat sperm cells (not shown). Weitrnan et al. have shown similar expression of the FRs on the epithelium of the human epididymis. Binding of the autoantibodies to the FRs can interfere with maturization of sperm cells, resulting in male sterility. The autoantibodies to the FRs can bind to these FRs, thereby blocking folate uptake by the cells. The resulting intracellular folate deficiency impairs the function of the epididymis thus contributing to infertility.

In another particular embodiment, the present invention is directed to a method of diagnosing a subject at risk for experiencing an unsuccessful in vitro fertilization procedure, by detecting the autoantibodies to the FRs in the subject.

According to the present invention, the FRs are expressed on the epithelial layer of the endometrium. In accordance with the present invention, serum autoantibodies to the FRs can impede viability of the early embryo by preventing the uptake of folate.

In an in vitro fertilization procedure, ova are harvested from the ovarian follicles by laparoscopic or transvaginal surgery. Several ova are selected and transferred to a petri dish for fertilization with the sperm. After about 2-3 days in culture, formed blastocysts are implanted into the uterine endometrium. Accordingly, if in vitro fertilization is planned, the donors of both the egg and the sperm should be tested for the autoantibodies to the FRs in their body fluids, preferably serum, by employing an assay or a method for identification or diagnosis of the autoantibodies to the FRs, as described in the present invention.

In still another particular embodiment, the present invention is directed to a method of diagnosing a subject at risk for neurologic disorders, e.g., dementia, by detecting the autoantibodies to the FRs in the body fluids of the subject.

Figure 10:
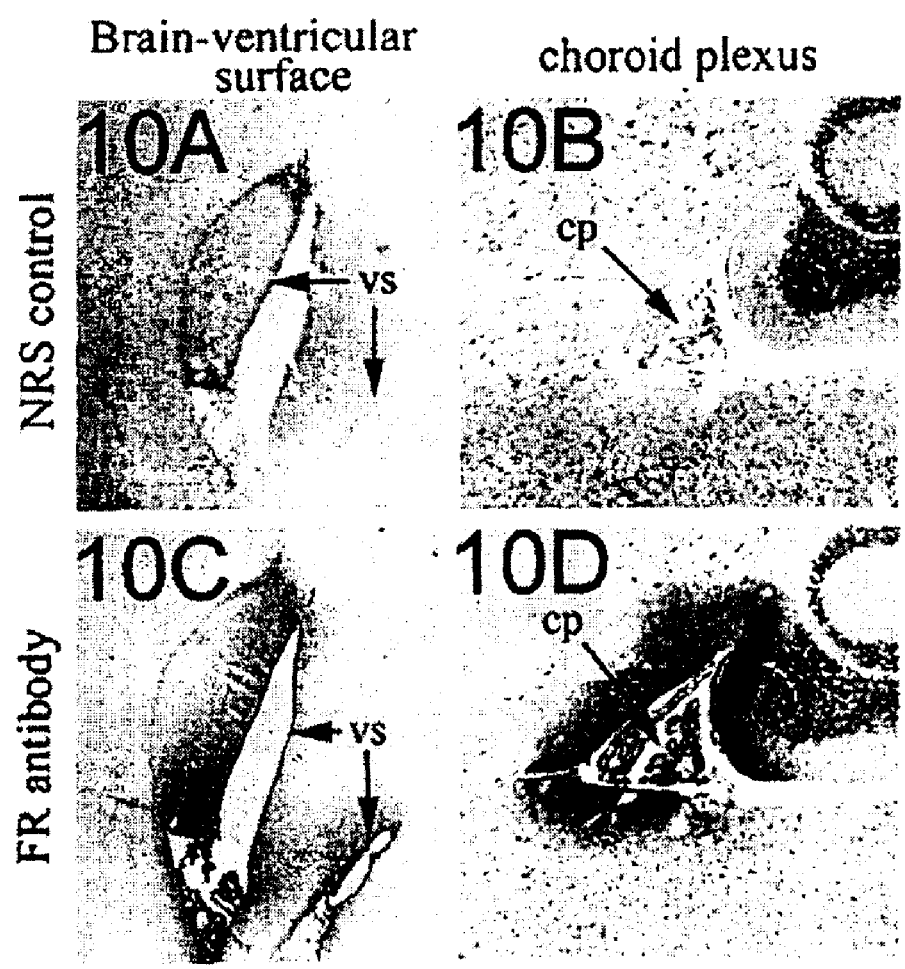
FIG. 10 Expression of FRs on brain ventricular surface and choroid plexus: shows the FRs that are expressed on the choroid plexus of the rat brain. Immunohistochemistry of brain tissue using a rabbit polyclonal antiserum to FRs. Normal Rabbit serum (NRS) served as the negative control. The brown color indicates the localization of the rabbit antibodies on the FRs. ventricular surface epithelium, vs; choroid plexus, cp.

According to the present invention, autoantibodies that block FRs can impair cellular uptake of folate. Since FRs are present on the choroid plexus (see FIG. 10), autoantibodies that block FRs can cause folate-sensitive neurological disorders, such as dementia, in men and women.

In yet another particular embodiment, the present invention is directed to a method of diagnosing a subject at risk for impaired folate absorption, by detecting the autoantibodies to the FRs in the body fluids of the subject, by employing an assay or a method for identification or diagnosis of the autoantibodies to the FRs, as described in the present invention.

Figure 11:
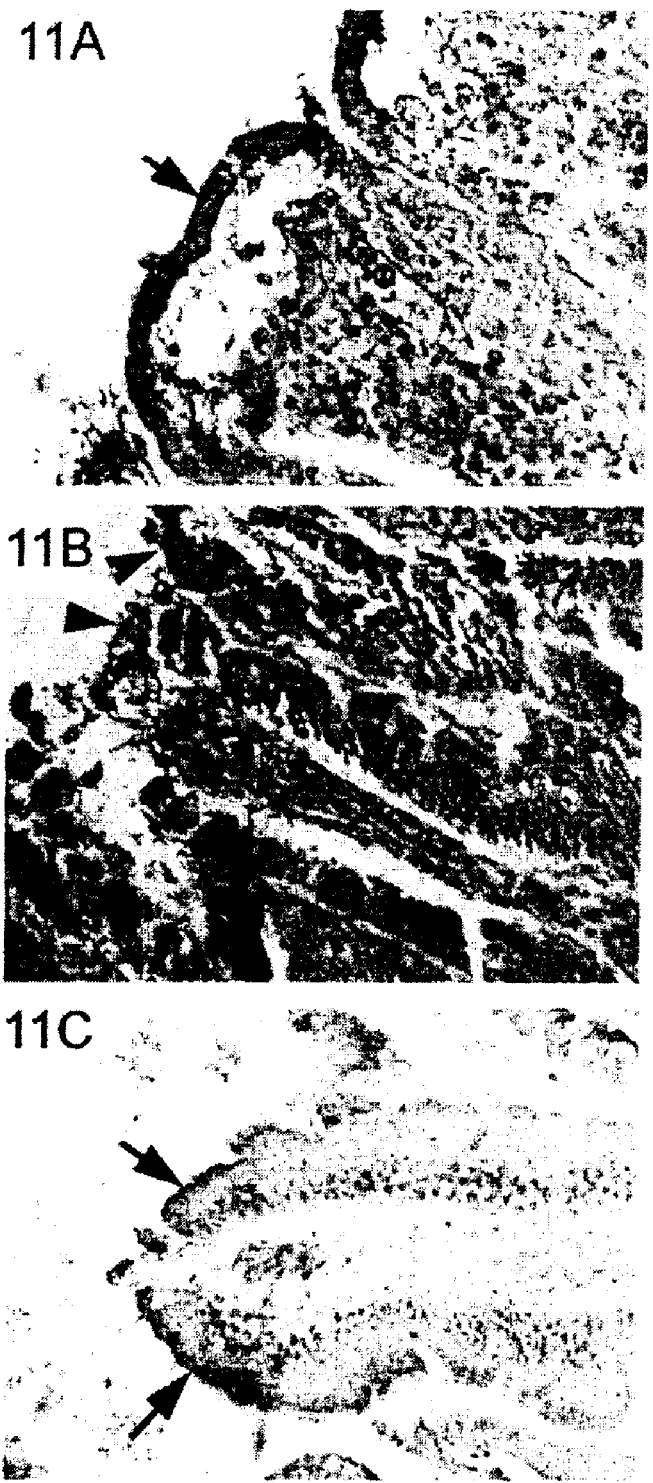
FIG. 11 Expression of FRs on small intestine: shows the FRs that are expressed on the intestinal mucosa of the rat. Immunostaining of the rat duodenum (A), jejunum (B) and ileum (C) with the rabbit serum containing antibodies to the rat FRs. Observe that the intensity of the immunostaining is most evident on the surface of the cells in the duodenum and jejunum (as indicated by the arrows) and substantially reduced on the surface of the ileum indicating diminished expression of the FRs in this region of the small intestine. Folates are absorbed predominantly in the proximal small intestine (duodenum and jejunum).

In addition, the presence of the FRs on the intestinal mucosa (see FIG. 11) demonstrates that autoantibodies that block the FRs can impair folic acid absorption.

In a further embodiment, the present invention is directed to a method for the prevention of folate-sensitive abnormalities or disorders in a subject including, but not limited to, neural tube defects (NTDs), infertility, spontaneous abortion, male sterility, unsuccessful in vitro fertilization, neurologic disorders and impaired folate absorption, comprising:
  a. detecting the presence of autoantibodies to FRs in a biological sample from the subject according to the methods described above, and
  b. administering pharmacologic folate supplements to the subject.

Thus, the present invention provides that the risk of having folate-sensitive abnormalities or disorders can be prevented or significantly reduced by pharmacologic folate supplementation.

According to the present invention, resorption of rat embryos induced by an antiserum to the FRs can be prevented by administration of folinic acid. For example, the inventors have discovered that administering an antiserum against the rat's FRs, such as antiserum generated in rabbits against the rat's FRs and injected to a pregnant rat, can induce resorption of early embryos and induce abnormalities that affect the brain and other organs, resulting in developmental defects during embryogenesis and fetal maturation (da Costa et al., *Birth Defects Research, Part A,* 67(10)837, (2003)).

The present inventors have determined that it is the anti-FRs antibodies that cause the embryonic resorptions and malformations in a subject, such as a rat. According to the present invention, purified FRs, e.g. FRα and FRβ from the mammalian placenta, e.g., the rat placenta, when coupled to a folate affinity matrix adsorb the specific anti-FRs antibodies from the antiserum. The specific antibodies to the FRs are removed by the folate affinity matrix to which the FRs has been attached (da Costa and Rothenberg). When a large dose of this adsorbed antiserum is administered to a gestational mammal, such as a rat, no resorption or structural abnormalities occur in the embryos that are examined on a later date.

Thus, blocking folate uptake by the antibody to the FRs causes resorptions and malformations of an embryo. According to the present invention, such resorptions and malformations of an embryo can be prevented by pretreatment of a subject with pharmacologic folate, such as folinic acid. For example, gestational rats were pretreated with a subcutaneous injection of folinic acid in an amount, for example, about 12 mg/kg in 3 divided doses. The pretreatment with folinic acid started one hour before the administration of a large dose of the antiserum, e.g., about 0.3 ml, with the folinic acid administered again on the following day. "A large dose" of an antiserum used herein refers to a dose that can consistently cause 100% resorption of an embryo within 48 hours. When gestational rats are administered with the folinic acid as indicated above, the embryos appear normal when examined 2 days later. However, when a larger dose of the antiserum, e.g., about 0.5 ml, is administered, folinic acid does not prevent injury to the embryos which are all resorbed in a short period of time, for example, 48 hours after antiserum administration.

Figure 6:
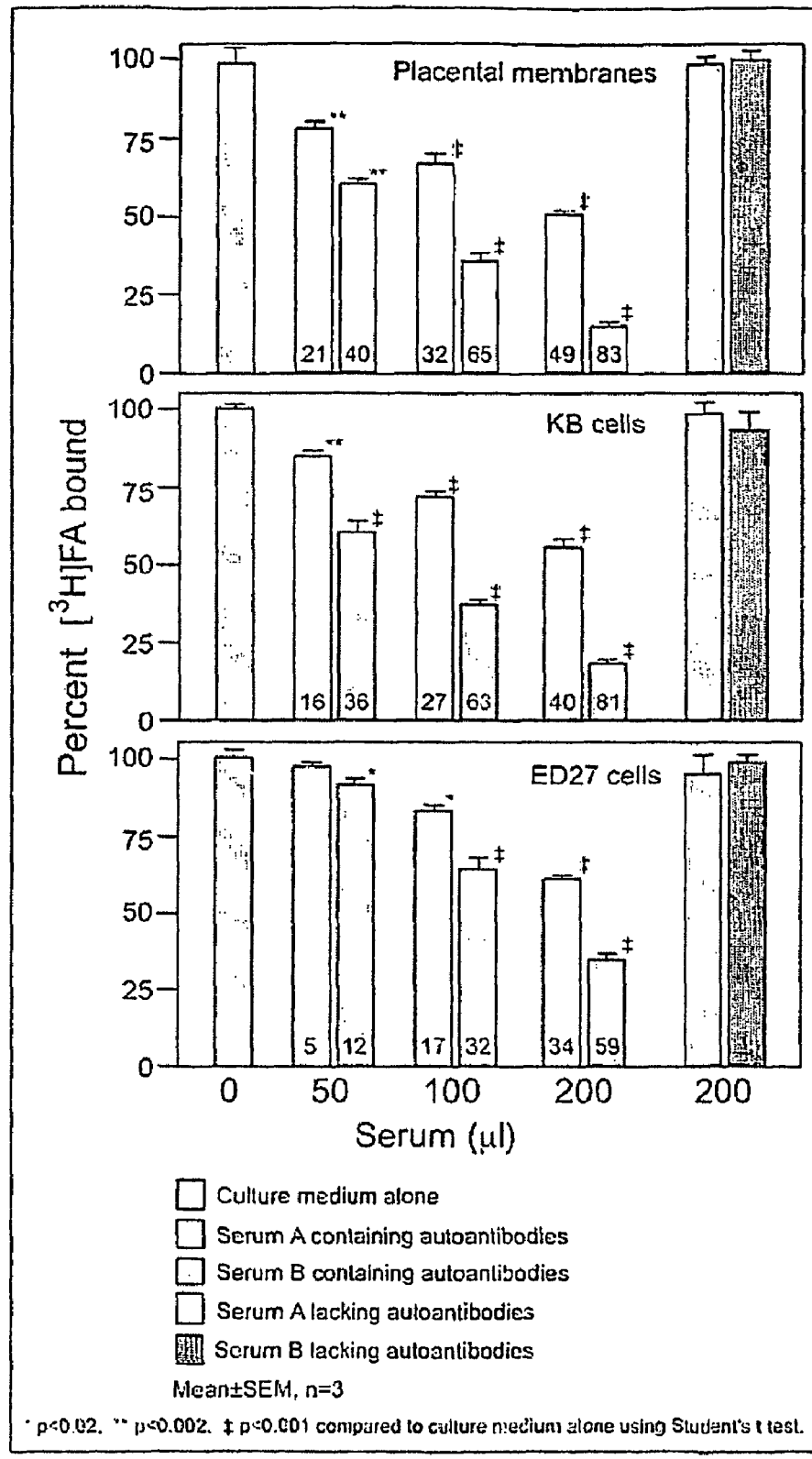
FIG. 6 Blocking of [$^3$H]FA Binding to FRs on Placental membranes, KB cells and ED27 cells by Serum Containing Blocking Autoantibodies to FRs: shows the ability of the autoantibodies to FRs to block the binding of folate to human placental membranes and to two human cultured cell lines (ED27 cells and KB cells). The number in each bar indicates the percent blocking by the autoantibodies of [$^3$H]FA binding to the apo-FRs on the cell membranes at 4° C. The methodology is described in Example 6.
Figure 7:
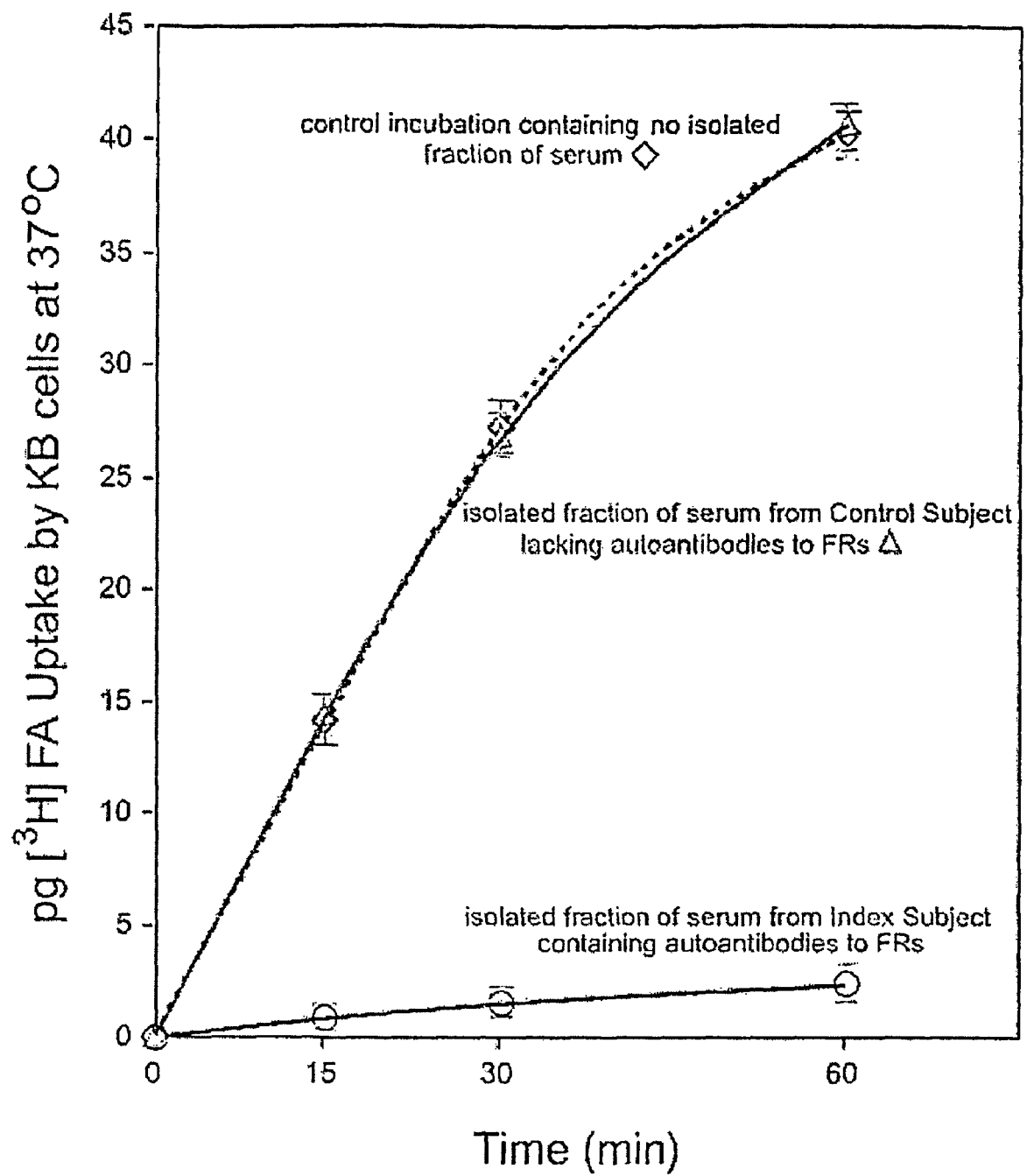
FIG. 7 Effect of Isolated Autoantibodies to the FRs on the Cellular Uptake of [$^3$H]FA by KB cells: shows the ability of the autoantibodies to FRs to block the uptake of folate by cultured KB cells. Autoantibodies to FRs were isolated from the serum of two Subjects as described in Example 7. KB cells were pre-incubated overnight at 37° C. with this isolated fraction of serum from either an Index Subject (contains FRs autoantibodies) (○), or a Control Subject (lacks FRs autoantibodies) (Δ). Following this incubation, the uptake of [$^3$H]FA by the KB cells was determined. A control incubation lacking the isolated fraction of serum is shown (◊). The I bars represent the SEM.

According to the present invention, autoantibodies that block FRs can impair cellular uptake of folate. For example, FIG. 6 demonstrates the ability of the autoantibody to the FRs to block the binding of folate to folate-receptors on two human cell lines and on human placental membranes. In addition, FIG. 7 shows the ability of autoantibodies to the FRs, isolated from the serum of a test subject, to block the uptake of folate at 37° C. by KB cells (a human cell line) in culture.

Accordingly, by administering an effective amount of pharmacologic folate to women having autoantibodies to the FRs, the risk for pregnancy with fetal complications, such as NTD, is significantly reduced in these women. It has been shown that supplementation of grain products with folic acid only reduces NTD occurrence by approximately 19%, while supplementation by daily ingestion of 0.8-4 mg of folic acid at the time of conception can reduce the occurrence rate of NTD by about 72%. According to the present invention, without intending to be bound by a particular theory, the different outcomes of these two approaches are believed to result from the lower amount of folate present in grain as compared to pharmacologic folate supplementation. It is further believed that folate-enriched grain does not contain a sufficient quantity of folic acid, whereas pharmacologic folate provides an amount sufficient to prevent the NTD at an early stage of embryogenesis.

Thus, a particular embodiment of the present invention provides a method that can detect the risk of a NTD pregnancy so that the disorder can be prevented or the risk can be significantly reduced by administering sufficient amounts of pharmacologic folate to the subject in need thereof.

Without intending to be bound by a particular theory, it is believed that the discovery that the serum from 9 of 12 women with a NTD complication contained the autoantibodies to the FRs provides substantial evidence that the autoantibodies to the FRs impairs embryogenesis by blocking folate uptake. It is also believed that the percentage of women who have autoantibodies in the test group (9/12 or 75%) corresponds to previous studies that showed a decrease of approximately 70% in the occurrence of NTD pregnancies with the start of daily supplementation with folic acid at the time of conception. It was reported that supplementation of grain products with folic acid only reduces NTD occurrence by approximately 19% (Honein et al, *JAMA*, 285(23):2981 (2001)), while supplementation of 0.8-4 mg of folic acid at the time of conception can reduce the occurrence rate of NTD by about 72%. It is believed that the different outcomes of these two approaches result from the lower amount of folate present in grain as compared to pharmacologic folate supplementation. It is believed that approximately 70% of NTD occurrences are due to interference of folate uptake by the autoantibodies to the FRs, while approximately 30% of NTD occurrences are not folate-responsive and may be the result of other well recognized causes, such as chemotherapeutic drugs, especially the antifolates, anti-epileptic drugs, chromosomal abnormalities, and environmental or genetic factors.

In accordance with the present invention, a woman who is identified as having the autoantibodies to the FRs in body fluids has an increased risk of having a pregnancy with a NTD fetus, or giving birth to a baby with folate-sensitive birth defects, such as NTDs. The woman should therefore take a pharmacologic amount of folate supplements when beginning a pregnancy to prevent dysmorphogenesis. A subject, whose body fluids have no detectable autoantibodies to the FRs, may still have some risk due to factors not related with the autoantibodies to the FRs. While large oral doses of folic acid can achieve striking reduction in the occurrence of birth defects, such as NTDs, grain fortified with folic acid can only achieve low-levels of reduction of the occurrence of NTDs. However, a woman beginning a pregnancy often does not take pharmacologic folate supplements, and thereby may necessarily increase the risk of dysmorphogenesis. Therefore, the present invention, for the first time, permits the identification of women who have an increased risk of dysmorphogenesis and therefore should take pharmacologic folate supplements, if the autoantibodies to the FRs is detected in their serum. Accordingly, a particular embodiment of the present invention provides a precise method for identifying a woman who requires folic acid supplementation thereby provides a clear guide for one who is planning a pregnancy as to whether or not she should take a pharmacologic folate supplement to prevent the risk of having a folate-sensitive abnormality or disorder. In accordance, a particular embodiment of the presentation provides a precise method for identifying a woman who requires folic acid supplementation. The method comprises identification or detecting autoantibodies to the FRs in a woman by employing an assay or a method described in the present invention, and notifying or alerting the woman having such autoantibodies that she should take folate supplements to avoid folate-sensitive abnormalities or disorders. The advantage of the method thereby provides a clear guide for one who starts a pregnancy as to whether or not she should take a pharmacologic folate supplement to prevent the risk of having a folate-sensitive abnormality or disorder. The assay for detecting the autoantibodies to the FRs in the serum of a woman who begins a pregnancy, by employing a method described above, is also encompassed by the present invention.

A particular embodiment of the present invention is directed to the prevention of folate-sensitive abnormalities, such as infertility, spontaneous abortion, male sterility, unsuccessful in vitro fertilization, neurologic disorders, or impaired folate absorption, by supplementing the diet of a subject having the risk for such abnormalities with an increased amount of folic acid or folinic acid, preferably, about 0.8 mg to about 4 mg daily.

According to the present invention, some of the risk of an unsuccessful in vitro fertilization procedure can be prevented. For example, if the autoantibodies to the FRs are found in the prospective female donor, she should start taking supplemental folic acid at the time the procedure is initiated to ensure adequate folate for the fertilized ovum at implantation. If the autoantibodies are found in both the prospective female and male donors, both parties should start taking supplemental folic acid at the time the procedure is initiated to ensure adequate folate for the fertilized ovum at implantation.

Figure 8:
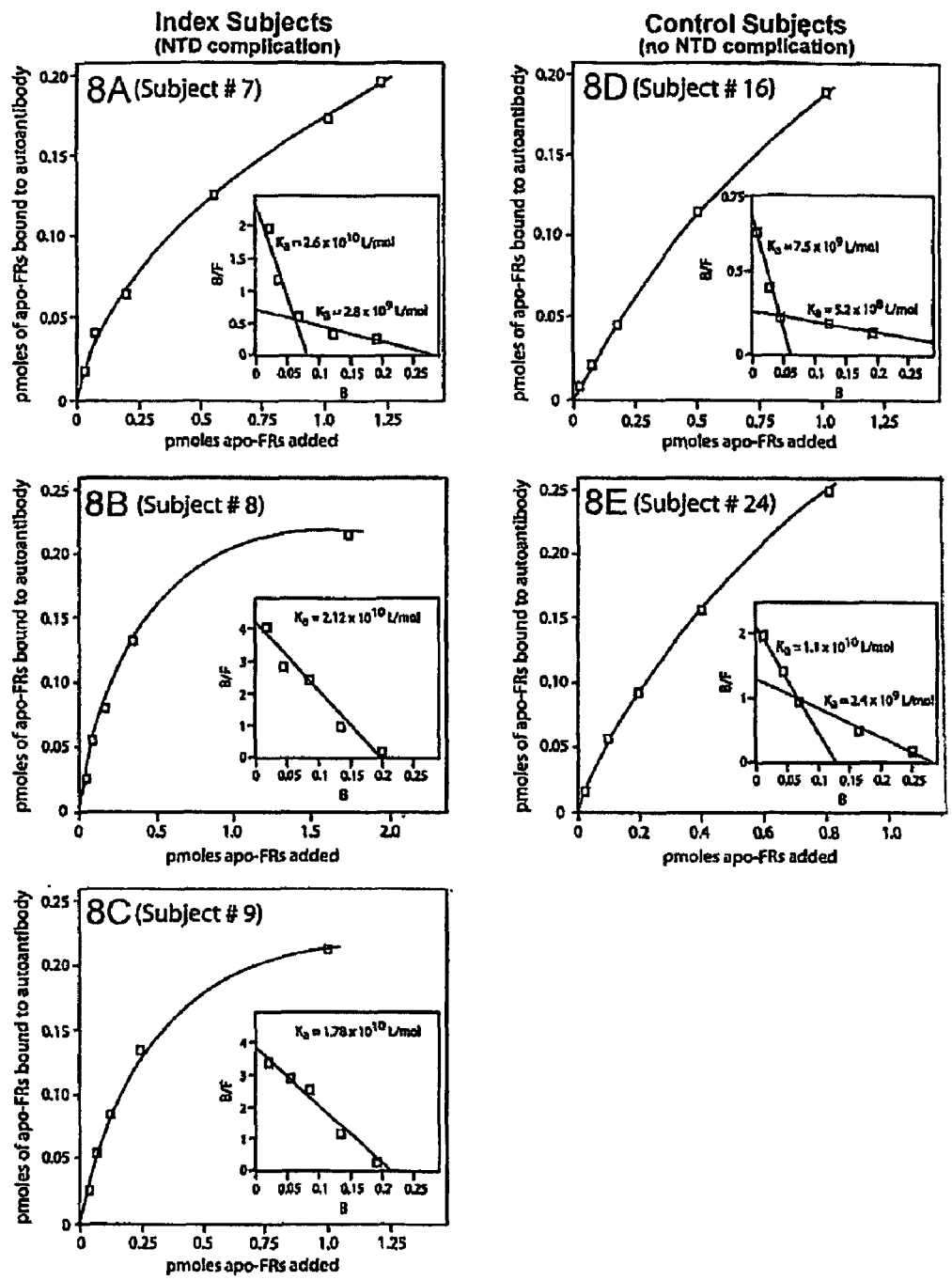
FIG. 8 Determination of the Binding Affinity of the Autoantibodies for the Folate Receptors: shows the graphic determination of the binding affinity constant ($K_a$) of the autoantibodies to FRs from the serum of five subjects. Placental membranes with apo-folate receptors were prepared as described in Methods and incubated overnight at 4° C. with the serum containing autoantibodies. [$^3$H]folic acid was then added and the fraction bound to the folate receptors was subtracted from the total folate binding capacity of the folate receptors to derive the pmoles of receptors blocked (B) per liter by the autoantibodies. The ratio of the autoantibody-blocked receptor to the free apo-receptor (B/F) was used for the Scatchard analysis, to compute the apparent association constant ($K_a$) which is shown in the inset.

Yet another embodiment of the present invention is directed to the determination of the titer of the circulating autoantibodies and the association constant ($K_a$) for the binding of the FRs by the autoantibody (see FIG. 8)

According to the present invention, without intending to be limited to any specific theory, it is believed that folate-sensitive congenital abnormalities, such as NTDs, are caused by autoantibodies to the FRs in the body of a pregnant mammal, such as an animal or a human. It is further believed that this effect is autoantibody-titer-dependent.

By "association constant" or "$K_a$" is meant an autoantibody's affinity for an antigen, preferably the FRs. $K_a$ is expressed quantitatively. According to the present invention, a high value for $K_a$ (e.g., $10^{10}$ L/mole) indicates a high affinity of the autoantibody for the FRs. In such an instance, it will be necessary to provide one having a determined high value $K_a$ with a higher dose of folic acid (or folinic acid) supplementation, e.g., to a woman at the time of conception, to circumvent the blocking of the folate binding sites on the membrane FRs by the autoantibodies to the FRs. For example, in accordance with the present invention, a daily intake of 4 mg of folic acid can raise plasma folate concentration sufficiently to provide cellular folate by diffusion or by dissociating the autoantibodies bound to the FRs. Conversely, a low $K_a$ value (e.g., $10^6$ L/mole) for the binding of the autoantibodies to the FRs would not cause a disease or disorder because folate has a higher affinity for the membrane folate receptors. Raising the plasma folate concentration with a smaller daily dose of folic acid (e.g., 1 mg/day) can displace the autoantibodies to the FRs from the folate receptors.

According to the present invention, a method for determining the $K_a$ for the interaction of a binding protein (such as an antibody) and a ligand (such as an antigen, e.g., a folate receptor) is described in Example 6. The determination of the $K_a$ for the blocking autoantibodies present in the serum of three of the index subjects who had NTD-complicated pregnancies and two of the control subjects is shown in FIG. 8.

Accordingly, a high titer autoantibody with high $K_a$, e.g., $10^{10}$ L/mole or higher, can induce severe immune reactions which can injure a conceptus and cannot be prevented by supplemental folinic acid or folic acid. In contrast, a low titer autoantibody with a lower $K_a$, e.g., $10^6$ L/mole or lower, would be folate-responsive and supplemental folinic acid or folic acid can be effective in preventing NTDs and/or other abnormalities, as described above. See also Example 1.

Thus, in a particular embodiment, the present invention is directed to the prevention of folate-sensitive abnormalities, for example, by supplementing with folic acid the diet of a woman having a risk of a pregnancy complicated by an abnormality such as a NTD, or by informing the woman and her obstetrician that the fetus be closely monitored with ultrasonography. According to the present invention, such ameliorative steps should be taken if the $K_a$ of the detected blocking autoantibody to the FRs is equal to or more than $10^9$ L/mole.

In a further embodiment, the present invention provides a test kit for detecting autoantibodies to the FRs in body fluids, e.g., serum, of a subject. By "test kit" is meant a package for commercial sale, containing materials needed for an assay. The test kit of the present invention comprises purified FRs described above, preferably non-aggregated FRs, reagents for treating (e.g. acidifying) serum samples from a subject, and at least one indicator which will detect a complex of autoantibodies to the FRs from the subject's serum and a purified FRs. A positive result indicates the presence of the autoantibodies to the FRs in a subject, thereby establishing an increased risk for the subject having infertility, spontaneous abortion, male sterility, unsuccessful in vitro fertilization procedure, neurologic disorders, or impaired intestinal absorption of folic acid, or having a pregnancy with fetal complications, such as NTDs.

Another test kit containing materials needed for detecting the presence of blocking autoantibodies in serum to the FRs, and determining the $K_a$ of these autoantibodies, is also contemplated by the present invention. The contemplated components and principles of the methodology of this test kit is illustrated in FIG. 9. This test kit comprises purified glycosylphosphatidylinositol (GPI)-FRs bound to a matrix (membrane, or via hydrocarbon chain or other hydrophobic matrix) or FRs covalently coupled to a matrix, folic acid (FA) coupled to a carrier (e.g. enzyme or radioactive label, or fluorescent marker, or biotin), and at least one indicator which will be used to detect the presence of the blocking autoantibodies in the subjects serum. The reduction in bound FAs obtained, which are coupled to a carrier, compared to the control incubation which is conducted in the absence of serum containing autoantibodies to the FRs indicates the presence of and provides the titer of the blocking autoantibodies to the FRs.

All the publications mentioned in the present disclosure are incorporated herein by reference. The terms and expressions which have been employed in the present disclosure are used as terms of description and not of limitation, and there is no intention in the use of such terms and expressions of excluding any equivalents of the features shown and described, or portions thereof, it being recognized that various modifications are possible within the scope of the invention.

The present invention is further illustrated by the following specific examples which are not intended in any way to limit the scope of the invention.

Example 1

Effects of Administering an Antiserum to FRs to Pregnant Rats

In the study, (da Costa et al., *Birth Defects Research, Part A*, 67(10)837, (2003)), titrated volumes of an antiserum raised in a rabbit to the rat FRs were injected into the peritoneal cavity of gestation day 8 rats and the embryos examined at a different time periods. Gestation day 8 rats were chosen because this is the period of marked growth and differentiation (i.e. organogenesis). Gestation day 8 is also the period of neurulation when the neural folds are forming but have not begun to fuse. The antiserum, which has a high titer for the binding of the FRs (1 ml of antiserum immunoprecipitates 12 ug of FRs) was administered in doses of 0.1-1 ml. The administration of 0.3-1 ml of the antiserum caused complete resorption of all the embryonic implants by gestation day 10; 0.27 ml and 0.25 ml of this antiserum induced resorption of approximately 50% of the embryos. The surviving embryos examined on gestation day 15 showed growth and developmental defects. Some of the embryos developed abnormalities of the central nervous system that resulted in internal hydrocephalus; abnormal cardiac and palate development were also observed. When smaller doses of the same antiserum, e.g. 0.1-0.2 ml, was administered to gestation day 8 rats, no identifiable abnormalities were observed in the fetuses examined on gestation day 17. There was no embryonic resorption or developmental abnormalities in control rats given 1 ml of normal rabbit serum (NRS).

To establish that the embryonic resorptions and malformations were caused specifically by the antibodies to the FR(s), purified FRα and FRβ isoforms from the rat placenta were coupled to the folate affinity matrix to adsorb the specific anti-FR antibodies from the antiserum. When about 0.4 ml and about 0.3 ml of the adsorbed antiserum was administered to gestation day 8 rats, no resorption or structural abnormalities occurred in any of the embryos examined on gestation day 20.

To determine whether the cause of the resorptions and malformations of the embryos were caused by blocking folate uptake by the antibodies to the FRs, rats on gestation day 8 were pretreated with subcutaneous injection of folinic acid (12 mg/kg) in 3 divided doses starting one hour before the administration of 0.3 ml of the antiserum (a dose that consistently caused 100% resorption of embryos within 48 hours), and again on the following day. The embryos examined 2 days later appeared normal after administration of folinic acid. However, when 0.5 ml of the antiserum was administered, the administration of folinic acid did not prevent injury to the embryos which were all resorbed by day 10. Microscopic examination of the embryonic tissue revealed evidence of inflammation indicating that an intense irreversible immunologic reaction injured the embryo. However, when dexamethasone, a steroid with anti-inflammatory properties, was administered before the administration of antiserum, the injury to the embryos was prevented.

Example 2

Purification of Folate Receptors from Human Placenta

1. Materials and Methods

[$^3$H]folic acid (FA) with a specific activity of 27.6 Ci/mmol was purchased from Moravek Biochemicals (Brea, Calif.); It was stored at −80° C. after determining its purity to be >95% by ZnSO$_4$ precipitation. Phenylmethylsulfonyl fluoride (PMSF), Trasylol and Norit A Charcoal were purchased from Sigma (St. Louis, Mo.). Ethylenediaminetetraacetic acid (EDTA) was obtained from Fischer Scientific. Triton X-100, and the complete scintillation cocktail, Cytoscint, were purchased from ICN Biochemicals. The Dc Protein assay kit, sodium dodecyl sulfate (SDS) and acrylamide were purchased from Bio-Rad (Richmond, Va.).

The concentration of the folate compounds was determined from their published extinction coefficients. The protein concentration was determined with the Dc Bio-Rad Protein Assay kit, which uses the modified Biuret method.

2. Purification of the FRs from Human Placentas

Human placentas were obtained from the Obstetrics Department of the hospital following a delivery. One hundred grams of the human placenta was homogenized in 300 ml of 0.01M sodium phosphate buffer, pH 7.4 containing 1.0 mM PMSF and 10 mM EDTA, using a polytron homogenizer. The resulting suspension was centrifuged at 40,000×g for 1 hour at 4° C. The pellet was washed three times by resuspension in the above buffer followed by centrifugation. The washed membrane pellet was suspended in the solubilization buffer (0.01 M sodium phosphate buffer, pH 7.4 containing 1.0 mM PMSF, 10 mM EDTA and 1% Triton X 100), and the proteins solubilized at 37° C. for 2 hours. Following solubilization, the suspension was centrifuged at 40,000×g for 1 hour at 4° C. The supernate pH was lowered to 3.5 with 1 N HCl and 4% dextran-coated charcoal was then added to adsorb the released endogenous folate. The charcoal was removed by centrifugation and the pH of the supernate that contains the apo-FRs was raised to 7.4 with the addition of 1 N NaOH. This preparation was then mixed at 25° C. for 1 hour with 1 ml of a folate affinity matrix that was prepared by coupling FA to epoxy-activated Sepharose 6B as previously described in an article by Sadasivan et al., *Biochim. Bioph. Acta.* 925:36-47 (1987). The affinity matrix was then pelleted at 3000 rpm for 5 min and washed with the following buffers: 1) 50 ml×3 with 0.01 M sodium phosphate buffer, pH 7.4 containing 1 mM PMSF, 10 mM EDTA and 0.1% Triton X-100, 2) 50 ml×3 with 0.1M sodium phosphate buffer, pH 7.4 containing 1 mM PMSF, 10 mM EDTA and 0.1% Triton X-100, 3) 50 ml×3 with 0.01 M sodium phosphate buffer, pH 7.4 containing 1 mM PMSF, 10 mM EDTA, 0.1% Triton X-100 and 1 M NaCl, and 4) 50 ml×3 with 0.01M sodium phosphate buffer, pH 7.4 containing 1 mM PMSF, 10 mM EDTA and 0.1% Triton X-100.

The FRs were dissociated from the affinity matrix by incubating it for 10 minutes in 1 ml of 0.1 M glycine buffer pH 3.0, containing 1 mM PMSF, 10 mM EDTA and 0.1% Triton X-100. The matrix was pelleted by centrifugation and the supernatant fraction was neutralized with 1 ml of 0.2 M veronal.

This process of acid elution of the FRs from the affinity matrix was repeated three times and the folate binding capacity of each eluate was determined using [$^3$H]FA as previously described (Luhrs et al., *Arch. Biochem. Biophys.* 250:94-105 (1986)). The purity of the FRs in this preparation was determined by SDS (10%) polyacrylamide gel electrophoresis (PAGE) and the gel was stained for protein with Coomassie brilliant blue. The purity of the FRs preparation was also determined by Western blotting using an antiserum generated in a rabbit immunized with the purified FRs.

3. Generating Non-Aggregated FRs

Non-aggregated FRs were generated by removing the glycosylphosphatidylinositol (GPI) adduct from the protein. The enzyme, glycosylphosphatidvlinositol specific phospholipase C, hydrolyzes the GPI adduct releasing the FR protein from the cell membrane (Other enzymes such as alkaline phosphatase and phospholipase D may also be used for this purpose). The FR was then isolated by binding to folic acid coupled to a matrix. After thorough washing of the matrix, the FR protein was released by acidification. The matrix was removed by centrifugation, and the pH of the supernatant fraction was raised to 7.4. This preparation of the FRs does not aggregate and can be used to coat the wells of the ELISA plates for assaying serum for the autoantibodies to the FRs.

Example 3

Procedure for Identifying Autoantibodies in the Serum to the Folate Receptors (FRs)

The rationale and steps in this procedure are summarized below:

1. Serum to be tested for autoantibodies against the FRs was acidified to pH 3.5 with 0.1 M glycine-HCl at room temperature to dissociate the endogenous folate from soluble FRs in the serum. This acidification also dissociated immunoreactive soluble FRs in the serum from the autoantibodies.
2. The dissociated folate was removed from the solution by adsorption to dextran (molecular weight 60,000-90,000) coated charcoal.
3. The FRs purified from the cell membranes isolated from human placenta (as described in Example 2) were incubated with [$^3$H]FA in 0.1 M sodium phosphate buffer, pH 7.4, to generate the [$^3$H]FA-FRs radiolabeled antigen. Sufficient [$^3$H]FA was added to provide a 10-20% excess over the FRs concentration.

4. To identify the autoantibodies in the serum to the FRs, the acidified serum (from step 1) was added to 0.2 M veronal, pH 8.9, containing the [$^3$H]FA-FRs in one test tube; and to a second test tube, a 10 to 20 fold greater concentration of unlabeled FA-FRs was added with the [$^3$H]FA-FRs. The pH of the reaction was approximately 8.6 and the samples were incubated for 24 hours at 4° C. At this pH, the excess free [$^3$H]FA rapidly binds to any soluble apo-FRs in the serum which then binds to the autoantibodies. If the complexing of the radiolabeled FRs with the autoantibodies was specific, this binding would be competed out by the excess unlabeled FA-FRs contained in the second tube.

5. After the overnight incubation, a *Staphylococcus* protein-A membrane suspension sufficient to bind all the IgG was added to the reaction and incubated at 4° C. for 10 minutes.

6. The samples were centrifuged at 6000 RPM for 3 min to pellet the protein-A with the bound IgG.

7. The supernatant fraction was removed and the pelleted membranes were washed 3 times with 0.01 M sodium phosphate buffer, pH 7.4, containing 0.05% Triton X-100.

8. The washed pellet was suspended in a scintillation cocktail or mixture and the radioactivity was measured in a scintillation counter.

9. The radioactivity in the [$^3$H]FA-FRs sample that was significantly greater than the assay containing the unlabeled folic acid bound to the FRs indicated that the serum being tested contained the autoantibodies. A quantitative estimate of the autoantibody titer was determined by the molar amount of radiolabeled folate bound to the receptor.

Result

Autoantibodies to the FRs were detected in 9 (Subject #1-#9) out of 12 women in the test group. Autoantibodies were identified in serum of 2 women (Subject #16 and #24) in the control group one of whom was pregnant. No autoantibody was identified in serum from the remaining 22 women in the control group, 18 of whom had a total of 20 normal pregnancies, and 4 were nulligravidas. See FIG. 1.

Example 4

Alternative Methods for Detection of Autoantibody-FRs Complex

Alternative methods to the Protein-A membranes to separate the free [$^3$H]FA-FRs antigen from the autoantibody-bound antigen include selective precipitation of the immune complex with ammonium sulfate, sodium sulfate, 50% ethanol, polyethylene glycol and an antibody raised in a rabbit or goat to the human IgG (or IgM).

Example 5

ELISA Assay Protocol

A Test kit to facilitate convenient analysis of biological samples for detecting the autoantibodies using the antigens (FRs) of the subject invention. Such kits can utilize recombinant or synthetic peptides, and the associated methods for ELISA and RIA technologies to detect autoantibodies that are already established.

For example, for the ELISA assay, the kit could contain the following components:

1. One or more of the FRs antigens of this invention;
2. Enzyme (e.g., peroxidase or alkaline phosphatase);
3. Conjugated anti-human immunoglobulin (animal: goat, rabbit etc.);
4. Positive and negative controls.

The above kit could include variations such as 96 well plates, calorimetric reagents, ELISA readers, blocking reagents, and wash buffers.

The kit described above may be modified to include any appropriate laboratory supplies. In addition to using immunoprecipitation techniques, the subject invention can be practiced utilizing any other procedures that could detect FRs autoantibodies. The principles and experimental methods of these procedures are well known to those skilled in the art. The assays can use natural or recombinant FRs which bind to the autoantibodies. Both whole cell and cell lysates may also be used to detect the FRs autoantibodies. The amino acid sequence of the FRs may be used to ascertain immunologically reactive epitopes which will react with the autoantibodies. These sequences can then be produced using recombinant peptides.

Purified protein or lysate of the cells producing the protein could also be used for the assays. In addition, it should be understood that the examples and embodiment described herein are for illustrative purposes only, and that various modifications or changes will be suggested to persons in the art and are to be included within the spirit and purview of this application and the scope of the appended claims.

Example 6

Determining the Presence of Blocking Autoantibodies in Serum to FRs

The effect of the autoantibodies on the binding of folate to FRs was determined using placental membranes and two cultured cell lines, ED27 cells derived from first trimester human placenta and KB cells derived from a human epidermoid carcinoma. The placental membranes were prepared by homogenizing human placenta in three volumes of 0.01 M sodium phosphate buffer, pelleting the membranes by centrifugation at 3000×g followed by three washes in the same buffer. The membranes were then suspended in 0.1 M acetic acid for 5 minutes to dissociate the folate bound to the FRs, washed three times to remove the dissociated folate, and then resuspended in 0.01M sodium phosphate buffer, pH 7.4, and the folate binding capacity per unit volume determined by the binding of [$^3$H]FA.

The placental membranes were used to determine the effect of the autoantibodies on the binding of [$^3$H]FA to the FRs by incubating 200 μl of a 1% suspension of the membranes with charcoal-treated test serum overnight at 4° C. The following day, the membranes were washed with ice cold PBS and [$^3$H]FA (125 pg) in 1 milliliter of PBS was added and the suspension incubated for 30 minutes at 40° C. The membranes were then washed with cold buffer, solubilized with 1 N NaOH and the radioactivity determined.

The ED27 and KB cells were each plated in triplicate at a density of 20,000 cells in 1.83 cm$^2$ wells containing folate deficient Dulbecco's Minimum Essential Medium with 10% fetal calf serum and the test serum, both of which were treated with charcoal to remove free endogenous folate, and incubated overnight at 37° C. The following day, the temperature of the wells was lowered to 4° C. and the cells washed three times with ice cold Hanks Balanced Salt Solution (HBSS).

[³H]FA (125 pg) in 1 milliliter of HBSS at 4° C. was then added to the wells and the incubation continued for 30 minutes, followed by three washes with 1 milliliter of cold HBSS. The cells were then lysed with 500 µl of 1 N NaOH and the radioactivity determined. Results of this assay is shown in FIG. 6.

Example 7

Determining the Presence of Autoantibodies to FRs that Block the Uptake of Folate by Cells in Culture For the folate binding and cellular uptake studies with the KB cells, the autoantibodies were isolated from the serum of a Test Subject using placental membranes that served as an affinity matrix to bind the autoantibodies to the FRs. Serum from a Control Subject lacking autoantibodies to the FRs was similarly treated. Ten milliliters of each serum sample was incubated with placental membranes (1 milliliter packed volume) overnight at 4° C. and then washed extensively with cold HBSS to remove the unbound components in the serum. The autoantibodies bound to FRs on the membranes were eluted by suspending the preparation for 5 minutes in 0.1 M acetic acid containing 0.1% bovine serum albumin, and this was repeated two additional times. The fractions were pooled and dialyzed against HBSS at 4° C. overnight. The final preparation was concentrated by vacuum dialysis overnight at 4° C.

The KB cells (20,000) were plated in duplicate in 3.5 cm² culture dishes and incubated overnight at 37° C. with the isolated autoantibodies. The control serum was similarly processed and incubated with the KB cells. As an additional control, the KB cells were incubated in medium lacking the isolated fraction of serum. The following morning, the cells were washed with HBSS and fresh medium containing [³H] FA (125 pg) was added to the wells and the incubation continued for 15, 30 and 60 minutes at 37° C., with a duplicate set incubated at 4° C. The cells were then washed with HBSS at 4° C., lysed with 500□l of 1 N NaOH and the radioactivity determined. The difference in the cell associated radioactivity at 4° C. and 37° C. represents the cellular uptake of the[³H] FA. The results are shown in FIG. 7.

Example 8

Determining the Association Constant ($K_a$) for the Binding of the [³H] Folic Acid-FR Complex by the Blocking Antibody to the FRs There are several methods for determining the $K_a$ for the interaction of a binding protein (such as an antibody) and a ligand (such as an antigen). A Scatchard plot (Scatchard, *Ann. N.Y. Acad. Sci.* 51: 660, (1949)) is one of a number of arithmetic methods to determine the $K_a$ value for the interaction of a protein and ligand. Berson and Yalow used this method to determine the $K_a$ for binding of insulin by antibodies generated to this hormone (Berson and Yalow, *J. Clin. Invest.* 38: 1996, (1959)).

Placental membranes with apo-FRs were prepared by homogenizing human placenta in three volumes of 0.01 M sodium phosphate buffer, pelleting the membranes by centrifugation at 3000×g followed by three washes in the same buffer. The membranes were then suspended in 0.1 M acetic acid for 5 minutes to dissociate the folate bound to the FRs, washed three times to remove the dissociated folate, and then resuspended in 0.01M sodium phosphate buffer, pH 7.4, and the folate binding capacity per unit volume determined by the binding of [³H]FA. This membrane preparation was incubated overnight at 4° C. with the autoantibodies to FRs from the serum of a subject. [³H]FA was then added and the fraction bound to the FRs was subtracted from the total folate binding capacity of the FRs to derive the pmoles of FRs blocked per liter by the autoantibodies. The ratio of the autoantibody-blocked receptor to the free apo-receptor was used for the Scatchard analysis, which is shown in the inset of FIG. 8.

What is claimed is:

1. A method for detecting the affinity of a folate receptor (FR) autoantibody in a subject, comprising:
   a. obtaining from a subject a biological sample suspected of comprising a FR autoantibody;
   b. providing an affinity matrix comprising apoFR;
   c. acidifying the biological sample;
   d. removing any unbound folic acid from the biological sample;
   e. contacting the affinity matrix with the biological sample under conditions suitable for forming an autoantibody-apoFR complex;
   f. dissociating and removing from the affinity matrix any apoFR-bound autoantibody;
   g. measuring the autoantibody's affinity for apoFR; and
   h. determining whether or not the dissociated autoantibody that was removed from the affinity matrix has an effect on folate uptake,
      wherein a value of about $10^{10}$ L/mole for an autoantibody's affinity for apoFR indicates a high affinity and a value of about $10^6$ L/mole for an autoantibody's affinity for apoFR indicates a low affinity.

2. The method of claim 1, wherein the affinity matrix comprising apoFR, is a cell membrane from a mammalian cell or tissue that produces apoFR.

3. The method of claim 2 wherein the cell or tissue is a human cell or tissue.

4. The method of claim 2 wherein the cell or tissue is placental.

5. The method of claim 2 wherein the cell is a cultured ED27 cell or a cultured KB cell.

6. The method of claim 1, wherein the affinity matrix comprises apoFR covalently coupled to the affinity matrix.

7. The method of claim 1, wherein the biological sample is the subject's serum.

8. The method of claim 1, wherein the biological sample is an extract of the subject's cell or tissue.

9. The method of claim 1, wherein determining the effect of the dissociated autoantibody on folate uptake in cells expressing FR comprises comparing the uptake of labeled folate in the presence and absence of the dissociated autoantibody.

10. The method of claim 9, wherein the effect of the dissociated autoantibody on folate uptake is determined in ED27 cells or KB cells.

* * * * *